United States Patent
Eastman et al.

(10) Patent No.: US 10,718,765 B2
(45) Date of Patent: Jul. 21, 2020

(54) BIOMARKERS AND METHODS FOR MEASURING AND MONITORING JUVENILE IDIOPATHIC ARTHRITIS ACTIVITY

(71) Applicant: Crescendo Bioscience, South San Francisco, CA (US)

(72) Inventors: Scott Eastman, South San Francisco, CA (US); Eric Sasso, South San Francisco, CA (US)

(73) Assignee: CRESCENDO BIOSCIENCE, INC., South San Francisco, CA (US)

( * ) Notice: Subject to any disclaimer, the term of this patent is extended or adjusted under 35 U.S.C. 154(b) by 46 days.

(21) Appl. No.: 15/282,562

(22) Filed: Sep. 30, 2016

(65) Prior Publication Data

US 2017/0016896 A1 Jan. 19, 2017

Related U.S. Application Data

(63) Continuation of application No. PCT/US2015/023302, filed on Mar. 30, 2015.

(60) Provisional application No. 61/974,390, filed on Apr. 2, 2014.

(51) Int. Cl.
| | |
|---|---|
| G01N 33/53 | (2006.01) |
| G01N 33/564 | (2006.01) |
| G09B 7/00 | (2006.01) |
| C12Q 1/6883 | (2018.01) |
| G16B 40/00 | (2019.01) |

(52) U.S. Cl.
CPC ......... *G01N 33/564* (2013.01); *C12Q 1/6883* (2013.01); *G09B 7/00* (2013.01); *C12Q 2600/118* (2013.01); *C12Q 2600/158* (2013.01); *G01N 2800/102* (2013.01); *G01N 2800/56* (2013.01); *G01N 2800/60* (2013.01); *G16B 40/00* (2019.02)

(58) Field of Classification Search
None
See application file for complete search history.

(56) References Cited

U.S. PATENT DOCUMENTS

| | | | |
|---|---|---|---|
| 4,230,797 | A | 10/1980 | Boguslaski et al. |
| 4,233,402 | A | 11/1980 | Maggio et al. |
| 4,275,149 | A | 6/1981 | Litman et al. |
| 4,376,110 | A | 3/1983 | David et al. |
| 4,659,678 | A | 4/1987 | Forrest et al. |
| 4,727,022 | A | 2/1988 | Skold et al. |
| 5,018,067 | A | 5/1991 | Mohlenbrock et al. |
| 5,744,305 | A | 4/1998 | Fodor et al. |
| 8,058,013 | B2 | 11/2011 | Karl et al. |
| 2002/0038227 | A1 | 3/2002 | Fey et al. |
| 2004/0122296 | A1 | 6/2004 | Hatlestad et al. |
| 2004/0122297 | A1 | 6/2004 | Stahmann et al. |
| 2005/0142569 | A1 | 6/2005 | Guild et al. |
| 2006/0094056 | A1 | 5/2006 | Chappell et al. |
| 2006/0286586 | A1 | 12/2006 | Drexhage et al. |
| 2007/0172888 | A1 | 7/2007 | Hallermayer et al. |
| 2008/0026485 | A1 | 1/2008 | Hueber et al. |
| 2009/0017472 | A1 | 1/2009 | Stuhlmuller et al. |
| 2009/0114627 | A1 | 5/2009 | Nakamura |
| 2009/0142792 | A1 | 6/2009 | Robinson et al. |
| 2009/0270272 | A1 | 10/2009 | Karl et al. |
| 2011/0137851 | A1 | 6/2011 | Cavet et al. |
| 2011/0251099 | A1 | 10/2011 | Visvanathan et al. |
| 2011/0269633 | A1 | 11/2011 | Bilello et al. |
| 2012/0258883 | A1 | 10/2012 | Chappell et al. |
| 2013/0052665 | A1 | 2/2013 | Ling et al. |
| 2014/0005071 | A1 | 1/2014 | Chappell et al. |
| 2014/0142861 | A1 | 5/2014 | Hagstrom et al. |

FOREIGN PATENT DOCUMENTS

| | | |
|---|---|---|
| JP | 2007506100 | 3/2007 |
| JP | 2008545960 | 12/2008 |
| JP | 2009524807 | 7/2009 |
| JP | 2010506147 | 2/2010 |
| JP | 2011520095 | 7/2011 |
| WO | 2004056456 | 7/2004 |
| WO | 2004088309 | 10/2004 |
| WO | 2005029091 | 3/2005 |
| WO | 2006125973 | 11/2006 |
| WO | 2007039280 | 4/2007 |
| WO | 2007085411 | 8/2007 |
| WO | 2007089303 | 8/2007 |
| WO | 2008037420 | 4/2008 |
| WO | 2009114627 | 9/2009 |
| WO | 2012061821 | 5/2012 |
| WO | 2013167727 | 11/2013 |
| WO | 2014118550 | 8/2014 |

(Continued)

OTHER PUBLICATIONS

Shimizu et al. 2013. Cytokine. 61:345-348.*
Schierbeck et al. (2013. J. Rheumatol. 40:1604-13.*
Johansen et al. 1999. Rheumatology. 38:618-626.*
Miller et al. 2011. Pediatric Rheumatology 9:9.*
Beukelman et al. 2011. 63:465-482 (Year: 2011).*
Petty et al. 2004. J. Rhematol. 31:390-392 (Year: 2004).*
Jeffrey R. 2010. Medicine 38:167-171 (Year: 2010).*
Pisetsky et al. 2012. Best Pract Res. Clin. Rheumatol. 26:251-261 (Year: 2012).*
Mallya R.K. et al., "Correlation of Clinical Parameters of Disease Activity in Rheumatoid Arthritis with Serum Concentration of C-Reactive Protein and Erythrocyte Sedimentation Rate", The Journal of Rheumatology (1982), vol. 9, No. 2, pp. 224-228.
Morel et al. (The Journal of Biol. Chem. (2002) vol. 277, pp. 34679-34691.

(Continued)

*Primary Examiner* — Shulamith H Shafer
(74) *Attorney, Agent, or Firm* — FisherBroyles, LLP; Victoria L. Boyd; Richard R. Eckman

(57) ABSTRACT

Biomarkers useful for assessing inflammatory disease or flare activity, in particular in juvenile idiopathic arthritis, are provided, along with kits for measuring expression of the biomarkers. The invention also provides predictive models, based on the biomarkers, as well as computer systems, and software embodiments of the models for scoring and optionally classifying samples.

7 Claims, 20 Drawing Sheets

(56) References Cited

FOREIGN PATENT DOCUMENTS

| WO | 2015132241 | 9/2015 |
|---|---|---|
| WO | 2015191423 | 12/2015 |

OTHER PUBLICATIONS

Mottonen et al., Arth. Rheum. 2002, 46(4):894-898.
Nadareishvili Z. et al., "Cardiovascular, Rheumatologic, and Pharmacologic Predictors of Stroke in Patients with Rheumatoid Arthritis: A Nested Case-Controlled Study", Arthritis Rheum. (2008), vol. 59, No. 8, pp. 1090-1096.
Partial European Search Report for Application No. 10824227.2, dated Jan. 12, 2015.
Pearson T.A. et al., "Markers of Inflammation and Cardiovascular Disease: Application to Clinical and Public Health Practice: A Statement for Healthcare Professionals From the Centers for Disease Control and Prevention and the American Heart Association", Circulation, 2003, pp. 499-511.
Pettit et al., Am. J. Pathol. 2001, 159:1689-99.
Pincus T. et al., "Relative Versus Absolute Goals of Therapies for RA: ACR 20 or ACR 50 Responses Versus Target Values for "Near Remission" of DAS or Single Measures", Clin. Exp. Rheum. (2004), vol. 22, Suppl. 35, pp. S50-S56.
Plant M.J. et al., "Relationship Between Time-Integrated C-Reactive Protein Levels and Radiologic Progression in Patients with Rheumatoid Arthritis", Arthritis & Rheumatism (2000), vol. 43, No. 7, pp. 1473-1477.
Prakken et al., "Juvenile idopathic arthritis", The Lancet, vol. 377, No. 9783, pp. 2138-2149 (2011).
Prevoo M.L.L. et al., "Modified Disease Activity Scores That Include Twenty-Eight-Joint Counts", Arthritis & Rheumatism (1995), vol. 38, No. 1, pp. 44-48.
Ranganath et al., J. Rheum. 2008, 35:1966-1971.
Ridker P.M. et al., "C-Reactive Protein and Other Markers of Inflammation in the Prediction of Cardiovascular Disease in Women", The New England Journal of Medicine (2000), vol. 342, No. 12, pp. 836-843.
Ritchlin, "Biomarker development in psoriatic arthritis", The Journal of Rheumatology, Vo. 89, pp. 57-60 (2012).
Senolt et al. (Ann. Rheum. Dis. (2007) vol. 66, pp. 458-461.
Smolen et al. (Arthritis Research Therapy (2008) vol. 10, pp. 208-219; Published May 2008).
Smolen et al., Arth. Rheum. 2005, 52(4): 1020-30.
Smolen S. et al., "A Simplified Disease Activity Index for Rheumatoid Arthritis for Use in Clinical Practice", Rheumatology (Oxford, 2003), vol. 42, pp. 244-257.
Sokka et al., Clin. Exp. Rheum. 2006, 24(Suppl. 43):S74-S76.
Stucki G. et al., "A Self-Administered Rheumatoid Arthritis Disease Activity Index (RADA) for Epidemiologic Research", Arthritis & Rheumatism (1995), vol. 38, No. 6, pp. 795-798.
Taylor et al., Arth. Rheum. 2004, 50(4):1107-1116.
Tibshirani, J. Royal Stat. Soc., series B 1996, 58(1):267-288.
Toonen et al. "Gene expression profiling in rheumatoid arthritis: Current concepts and future directions", Annals of the Rheumatic Diseases 200812 GB, vol. 67, No. 12, Dec. 2008, pp. 1663-1669.
Van den Berg et al., Arth. Rheum. 2005, 52:995-999.
Van Den Broek et al. "The evolution of biomarkers in rheumatoid arthritis: From clinical research to clinical care", Expert Opinion on Biological Therapy 200811 GB, vol. 8. No. 11, Nov. 2008, pp. 1773-1785.
Van der Heijde et al., Ann. Rheum. Dis'. 1990, 49(11):916-920.
Van Gestel A.M. et al., "Validation of Rheumatoid Arthritis Improvement Criteria That Include Simplified Joint Counts", Arthritis & Rheumatism (1998), vol. 41, No. 10, pp. 1845-1850.
Van Leeuwen et al., Br. J. Rheum. 1993, 32(suppl.):9-13.
Van Tuyl et al., Ann. Rheum. Dis'. 2008, 67:1574-1577.
Vasan, Circulation 2006, 113(19):2335-2362.
Verstappen S.M.M. et al., "Intensive Treatment with Methotrexate in Early Rheumatoid Arthritis: Aiming for Remission. Computer Assisted Management in Early Rheumatoid Arthritis (CAMERA, an Open-Label trategy Trial)", Ann. Rheum. Dis. (2007), vol. 66, pp. 1443-1449.
Visser, H. et al., "How to Diagnose Rheumatoid Arthritis Early: A Prediction Model for Persistent (Erosive) Arthritis," Arthritis & Rheumatism, Feb. 2002, pp. 357-365, vol. 46, Issue 2. May be Retrieved at <URL:http://onlinelibrary.wiley.com/doi/1 0.1 002/art.1 0117/pdf.
Visvanathan et al., "Inflammatory biomarkers, disease activity and spinal disease measures in patients with ankylosing spondylitis after treatment with infliximab", Annals of the Rhuematic Diseases, vol. 67, Issue 4, pp. 511-517 (2008).
Afuwape et al. (Histol. Histopathol. (2002) vol. 17, pp. 961-972.
Aletaha et al., Arth. Rheum. 2005, 52(9)2625-2636.
Baecklund et al., Arth. Rheum. 2006, 54(3):692-701.
Banerjee et al., Am. J. Cardiol. 2008, 101(8):1201-1205.
Benjamini and Hochberg. J. Royal Stat. Soc. B 1995 57(1):289-300.
Berk, "Statistical Learning from a Regression Perspective," Springer, 2008, p. 213.
Breedveld et al., Arth. Rheum. 2006, 54(1):26-37.
Breiman, Machine Learning 2001, 45(1):5-32.
Brown et al., Arth. Rheum. 2006, 54:3761-3773.
Brown et al., Arth. Rheum. 2008, 58(10)2958-2967.
Busquets-Perez et al., "Emerging drugs for axial spondyloarthritis including ankylosing spondlyitis", Expert Opinion on Emerging Drugs, vol. 18, No. 1, pp. 71-86 (2013).
Chan et al., "Evidence-Based Rheumatology", ed. M. Matucci Cerinic. Exp. Rheum. (2002), vol. 20, No. 4, pp. 443-444.
Chandran, "Soluble biomarkers may differentiate psoriasis from psoriatic arthritis", The Journal of Rheumatology, vol. 89, pp. 65-66 (2012).
Chinese First Office Action, Chinese Application No. 201080057651. 4, dated Jun. 21, 2013, 14 pages.
Chinese Second Office Action, Chinese Application No. 201080057651. 4, dated Jan. 13, 2014, 8 pages.
Churchman et al., Ann. Rheum. Dis'. 2009, 68:A1-A56, Abstract A77.
Coffman et al. Critical Reviews in Clinical Laboratory Sciences (2008) vol. 46, No. 6, pp. 531-562.
Cohen et al., Ann. Rheum. Dis'. 2007, 66:358-363.
Duurland et al., "Current developments in the use of biomarkers for juvenile idiopathic arthritis", Current Rheumatology Reports, vol. 16, No. 3, Article No. 406, pp. 1-6 (Epub. Jan. 21, 2014).
European Communication Response from Application No. 10824227. 2, dated Oct. 26, 2015.
Extended European Search Report for Application No. 10824227.2, dated May 8, 2015.
Felson d.T. et al., "The American college of Rheumatology Preliminary Core Set of Disease Activity Measures for Rheumatoid Arthritis Clinical Trials", Arthritis & Rheumatism (1993), vol. 36, No. 6, pp. 729-740.
Felson d.T. et al., "The American College of Rheumatology: Preliminary Definition of Improvement in Rheumatoid Arthritis Clinical Trials", Arthritis & Rheumatism (1995), vol. 38, No. 6, pp. 727-735.
Fransen J. et al., "Validity of the Disease Activity Score in Undifferentiated Arthritis", Arthritis Care and Research (2010), vol. 62, No. 10, pp. 1392-1398.
Goekoop-Ruiterman et al., Ann. Rheum. Dis. 2009 (Epublication Jan. 20, 2009).
Goekoop-Ruiterman et al., Arth. Rheum. 2005, 52:3381-3390.
Goodson et al., Ann. Rheum. Dis. 2005, 64(11):1595-1601.
Gossec L. et al., "Prognostic Factors for Remission in Early Rheumatoid Arthritis: A Multiparameter Prospective Study", Ann. Rheum. Dis. (2004), vol. 63, No. 6, pp. 675-680.
Green et al. (Rheumatology (2003) vol. 42, pp. 83-88).
Grigor C. et al., "Effect of a Treatment Strategy of Tight Control Rheumatoid Arthritis (the TICORA Study): A Single-Blind Randomised Controlled Trial", Lancet (2004), vol. 364, pp. 263-269.
Guler-Yuksel M. et al., "Changes in Hand and Generalised Bone Mineral Density in Patients with Recent-Onset Rheumatoid Arthritis", Ann. Rheum. Dis. (2009), vol. 68, pp. 330-336.

(56) References Cited

OTHER PUBLICATIONS

Hueber et al. (Arthritis & Rheumatism (2005) vol. 52, pp. 2645-2655).
International Preliminary Report on Patentability from Application No. PCT/US2010/052970, dated Dec. 16, 2010.
International Preliminary Report on Patentability from Application No. PCT/U52015/023302, dated Oct. 13, 2016.
International Preliminary Report on Patentability from Application No. PCT/US2015/034631, dated Dec. 22, 2016.
International Preliminary Report on Patentability from Application No. PCT/US2015/034945, dated Dec. 22, 2016.
International Search Report and Written Opinion from Application No. PCT/US2010/052970, dated Dec. 16, 2010.
International Search Report and Written Opinion from Application No. PCT/US2015/023302, dated Jun. 25, 2015.
International Search Report from Application No. PCT/US2015/034631, dated Aug. 28, 2015.
International Search Report from Application No. PCT/US2015/034945, dated Aug. 24, 2015.
International Search Report from Application No. PCT/US2016/054323, dated Dec. 8, 2016.
Japanese Office Action, Japanese Application No. 2012-534431, May 28, 2014, 14 pages.
Jarvis J. et al., "Gene-Expression Profiling: Time for Clinical Application", Lancet (2005), vol. 365, pp. 199-200.
Khan N.A, et al., "Duration of Morning Stiffness in the Assessment of Rheumatoid Arthritis Activity: A Questionable Issue", (Abstract) ACR/ARHP Scientific Meeting (2008), 1 page.
Kievit et al., Ann. Rheum. Dis'. 2008, 67(9):1229-1234.
Klooster et al. (Arthritis Research Ther. (2005) vol. 7, pp. R127-R138).
Kroot E.J.A. et al., "The Prognostic Value of Anti-Cyclic Citrullinated Peptide Antibody in Patients with Recent-Onset Rheumatoid Arthritis", Arthritis & Rheumatism (2000), vol. 43, No. 8, pp. 1831-1835.
Lipsky et al., iV. Engl. J. Med. 2000, 343:1594-1602.
Makinen et al., Ann. Rheum. Dis. 2005, 64(10):1410-1413.
Maksymowych et al., "Preliminary assessment of a multi-biomarker disease activity test for axial spondylorarthritis", In: 2014 American College of Rheumatology/The Association of Rheumatology Health Professionals (ACR/ARHP) Annual Meeting, Boston, MA, poster No. 2615 (Nov. 18, 2014).
Australian Office Action from Application No. 20110306593, dated May 1, 2015.
Australian Office Action from Application No. 20110306593, dated Dec. 2, 2014.
Australian Office Action Response from Application No. 2010306593, dated Feb. 19, 2015.
Canadian Office Action from Application No. 2,777,800, dated Nov. 7, 2016.
Canadian Office Action from Application No. 2,777,800, dated Sep. 14, 2017.
Canadian Office Action from Application No. 2,777,800, dated Dec. 21, 2015.
Canadian Office Action Response from Application No. 2,777,800, dated Jun. 16, 2016.
Canadian Office Action Response from Application No. 2,777,800, dated Apr. 28, 2017.
Centola et al., PLoS One, 2013, vol. 8, No. 4, pp. e606635.
Consolaro et al., Arthritis & Rheumatism, 2009, vol. 61, No. 5, pp. 658-666.
European Communication from Application No. 10824227.2, dated May 29, 2017.
European Communication Response from Application No. 10824227.2, dated Sep. 25, 2017.
European Communication Response from Application No. 15772723.1, dated Apr. 12, 2017.
European Communication Response from Application No. 15806913.8, dated Jun. 6, 2017.
Extended European Search Report for Application No. 15772723.1, dated Jul. 28, 2017.
International Search Report from Application No. PCT/US2016/054318, dated Jan. 13, 2017.
International Search Report from Application No. PCT/US2017/020181, dated Jun. 12, 2017.
Japanese Office Action from Japanese Application No. 2012-534431, dated Sep. 8, 2014.
Japanese Office Action Response from Japanese Application No. 2012-534431, dated Aug. 14, 2014.
Japanese Office Action Response from Japanese Application No. 2012-534431, dated Oct. 17, 2014.
Partial European Search Report for Application No. 15806913.8, dated Nov. 10, 2017.
Pedersen et al., Annals of the Rheumatic Diseases, 2011, vol. 70, No. 8, pp. 1375-1381.
Ringold et al. Annals of the Rheumatic Diseases, 2014, vol. 73, No. Suppl. 2, pp. 587.3-588.
Ringold et al., Arthritis & Rheumatology, 2014, vol. 66, pp. S10-S11.
Tilleman et al., Protea, 2005, vol. 5, No. 8, pp. 2247-2257.
Canadian Office Action Response from Application No. 2,777,800, dated Mar. 14, 2018, 52 pages.
European Communication from Application No. 10824227.2, dated Mar. 9, 2018, 9 pages.
European Communication Response from Application No. 10824227.2, dated May 10, 2018, 3 pages.
International Preliminary Report on Patentability from Application No. PCT/US2016/054323, dated Apr. 12, 2018, 13 pages.
European Communication Response from Application No. 16852551.7, dated Oct. 31, 2018, 2 pages.
Weinblatt et al., N. Engl. J. Med. 1999, 340:253-259.
Wisiowska et al. (Rheumatol. International (2007) vol. 27, pp. 947-954).
Wolfe F., "Comparative Usefulness of C-Reactive Protein and Erythrocyte Sedimentation Rate in Patients with Rheumatoid Arthritis", The Journal of Rheumatology (1997), vol. 24, No. 8, pp. 1477-1485.
Wolfe F., A Reappraisal of HAQ Disability in Rheumatoid Arthritis & Rheumatism (2000), vol. 43, No. 12, pp. 2751-2761.
Zatarain and V. Strand, Nat. Clin. Pract. Rheum. 2006, 2(11):611-618 (Review).
Zou, J. Royal Stat. Soc., series B 2005, 67(2):301-320.
Wells, G. et al., "Validation of the 28-Joint Disease Activity Score (DAS28) and European League Against Rheumatism Response Criteria Based on C-Reactive Protein Against Disease Progression in Patients with Rheumatoid Arthritis, and Comparison with the DAS28 Based on Erythrocyte Sedimentation Rate," Ann Rheum Dis., Jun. 2009;68(6):954-60. doi: 10.1136/ard.2007.084459. Epub May 19, 2008.

* cited by examiner

| Biomarker Concentration (log10 pg/mL) | JADAS-10 | Physician's Global | Parent Assessment of Child's Global Health | Total number of Joints with Active Arthritis | ESR |
|---|---|---|---|---|---|
| MBDA | 0.77 | 0.71 | 0.62 | 0.62 | 0.87 |
| IL-6 | 0.83 | 0.77 | 0.72 | 0.72 | 0.59 |
| MMP3 | 0.77 | 0.72 | 0.69 | 0.66 | 0.57 |
| CRP | 0.73 | 0.70 | 0.57 | 0.57 | 0.81 |
| TNF-RI | 0.71 | 0.68 | 0.56 | 0.66 | 0.62 |
| CALPROTECTIN | 0.68 | 0.62 | 0.53 | 0.56 | 0.73 |
| YKL-40 | 0.68 | 0.65 | 0.66 | 0.63 | 0.49 |
| ICAM-1 | 0.66 | 0.63 | 0.58 | 0.60 | 0.53 |
| SAA | 0.66 | 0.62 | 0.53 | 0.49 | 0.76 |
| VCAM-1 | 0.62 | 0.59 | 0.51 | 0.62 | 0.44 |
| MMP1 | 0.61 | 0.55 | 0.52 | 0.57 | 0.64 |
| IL8 | 0.58 | 0.53 | 0.47 | 0.56 | 0.46 |
| Resistin | 0.53 | 0.51 | 0.50 | 0.44 | 0.39 |
| VEGF | 0.51 | 0.46 | 0.43 | 0.55 | 0.49 |
| IL-1B | 0.38 | 0.29 | 0.31 | 0.37 | 0.46 |
| MDC | 0.23 | 0.23 | 0.03 | 0.14 | 0.10 |
| IL-6R | 0.19 | 0.21 | 0.14 | 0.21 | 0.08 |
| Leptin | 0.12 | 0.08 | 0.00 | 0.12 | 0.21 |
| EGF | 0.06 | 0.13 | 0.14 | 0.16 | -0.20 |
| PSE Algorithm #1 | 0.85 | 0.80 | | | |
| PSE Algorithm #2 | 0.85 | 0.81 | | | |

BIOMARKERS AND METHODS FOR MEASURING AND MONITORING JUVENILE IDIOPATHIC ARTHRITIS ACTIVITY

CROSS-REFERENCE TO RELATED APPLICATIONS

This application is related to and claims the benefit of International Application Serial No. PCT/US2015/023302, filed Mar. 30, 2015. The present application and International Serial No. PCT/US2015/023302 are related to and claim the priority benefit of U.S. Provisional Application No. 61/974,390, filed on Apr. 2, 2014, which is herein incorporated by reference in its entirety for all purposes.

FIELD OF THE INVENTION

The invention generally relates to a molecular classification of disease and particularly to genes and gene signatures for measuring and monitoring juvenile idiopathic arthritis.

BACKGROUND

This application is directed to the fields of bioinformatics and inflammatory and autoimmune diseases, with Juvenile Idiopathic Arthritis (JIA) as an example of these diseases. The present teachings relate to methods and compositions for assessing, diagnosing, monitoring, assessing disease and flare activity, and selecting treatment for inflammatory disease and autoimmune disease; e.g., JIA.

JIA is the most common rheumatic disease affecting children and adolescents. The annual incidence rate of pediatric rheumatic diseases is estimated to be 1 per 1,000 children, with an estimated prevalence of 50,000 to 70,000 children with JIA in the United States (Harrold et al., *J. Rheumatology* 40:1218-1225 (2013); Helmick et al., *Arthritis and rheumatism* 58:15-25 (2008); Weiss and Ilowite, *Juvenile idiopathic arthritis* 52:413-42 (2005)). JIA encompasses seven categories of disease, which include oligoarticular JIA (50-60% of cases), polyarticular rheumatoid factor (RF) positive JIA (5-10%), polyarticular RF negative JIA (30-50%), systemic JIA (10-20%), psoriatic JIA (2-15%), enthesitis-related arthritis (1-7%), and undifferentiated arthritis (5-10%) (Duffy et al., *Arthritis and rheumatism* 52:382-5 (2005); Weiss (2005)). Presentation, severity, and course of disease vary widely, from a benign self-limiting course, to severe, unremitting disease resulting in progressive joint destruction, skeletal deformity, growth retardation, possible blindness, and long-term disability (Packham and Hall, *Rheumatology* 41:1428-1435 (2002)).

Recent advances have expanded the treatment options available for treatment of JIA (Ruth and Passo, *Therapeutic Advances in Musculoskeletal Disease* 4:99-110 (2005)). Biologic agents targeting TNF, interleukin (IL)-1 receptor, and T-cell co-stimulation receptors are approved for JIA (Packman and Hall (2002)). Treatment goals for childhood arthritis are thus becoming more aggressive, with remission of the disease as the expectation. However, remission rates differ in frequency and durability between JIA categories even with the use of biologic treatments (Adib et al., *Rheumatology* 44:995-1001 (2005); Hyrich et al., *Rheumatology* 49: 116-22 (2010)).

Current therapeutic approaches to JIA are hindered by lack of good outcome measures. Despite substantial efforts, no validated, continuous measure of disease activity has been identified that clinicians can use to monitor disease status in individual patients, develop standards of care, assess quality of care, or use as a clinical trial end point (Wallace et al., *Arthritis care & research* 63: 929-36 (2011)). The 1997 American College of Rheumatology pediatric improvement criteria (ACR Pediatric 30) established a core set of outcome values for clinical trials (Giannini et al., *Arthritis and rheumatism* 40:1202-1209 (1997)) that include physician global assessment of disease activity (MD global), parent/child global assessment of well-being (PGA), functional ability (also known as CHAQ, Child/Parent Health Assessment Questionnaire), active arthritic joint counts and Westergren erythrocyte sedimentation rate (ESR). However, the ACR Pediatric 30 measures the degree of improvement from baseline and its use is limited to clinical trials for measuring minimal therapeutic efficacy for new medications. The more recently developed Juvenile Arthritis Disease Activity Score (JADAS) is a composite tool that includes four core variables of the ACR Pediatric 30: MD global, PGA, active joint counts, and ESR (Consolaro et al., *Arthritis and rheumatism* 61: 658-66 (2009)). Additional JADAS versions have been proposed, including a version that uses the C-reactive protein (CRP) in place of the ESR and one that does not include any measure of inflammation (Nordal et al., *Annals rheumatic disease* 71: 1122-7 (2012)). Both the JADAS and composite disease activity measures developed for adult RA (e.g., Disease Activity Score (DAS), DAS28, Clincial Disease Activity Index (CDAI), Simplified Disease Activity Index (SDAI)) have shown validity as measures for JIA disease state (Ringold et al., *Arthritis care & research* 62:1095-102 (2010)); Consolaro et al., *Arthritis and rheumatism* 61:658-66 (2009)). However, while the JADAS and RA composite measures hold promise for use in routine pediatric practice, these measures may misclassify active disease as inactive (Ringold (2010)). Furthermore, discordance has been reported between various core measures (MD global, PGA, and CHAQ) used to assess disease activity and functional ability in JIA patients (Consolaro et al., *J. Rheumatology* 34: 1773-76 (2007); Ravelli (2001); Giannini et al., *Arthritis and rheumatism* 40: 1202-1209 (1997)).

Accurate, ongoing evaluation of disease activity is critical for optimally managing JIA, to minimize the joint damage and long-term functional disability that can result from persistent active disease. To achieve the maximum therapeutic benefits for individual subjects, it is important to be able to specifically quantify and assess the subject's disease activity at any particular time, determine the effects of treatment on disease activity, and predict future outcomes. No existing single biomarker or multi-biomarker test produces results demonstrating a high association with level of HA disease activity. The embodiments of the present teachings identify multiple serum biomarkers for the accurate clinical assessment of disease activity in subjects with chronic inflammatory disease, such as JIA, along with methods of their use.

SUMMARY

The present teachings relate to biomarkers associated with inflammatory disease, and with autoimmune disease, including JIA, and methods of using the biomarkers to measure disease activity in a subject.

In an embodiment of the invention, a method for monitoring the presence or absence of juvenile idiopathic arthritis (JIA) disease activity in a subject, or for predicting flare activity in a subject having JIA is provided. The method comprises providing a test sample comprising a sample of bodily fluid taken from the mammal; determining sample concentrations for three or more biomarkers selected from the group consisting of alpha-2-macroglobulin (A2M); amyloid P component, serum (SAP); angiopoietin 1 (AGP1) antithrombin III (ATIII); ataxia telangiectasia mutated (ATM); B-cell activating factor (BAFF); chemokine (C-C motif) ligand 2 (CCL2); chemokine (C-C motif) ligand 3 (CCL3); chemokine (C-C motif) ligand 11 (CCL11); chemokine (C-C motif) ligand 22 (CCL22); chemokine (C-X-C motif) ligand 9 (CXCL9); chemokine (C-X-C motif) ligand 10 (CXCL10); CD40 ligand (CD40LG); C-reactive protein (CRP); complement C3; complement C4; complement factor H (CFH); epidermal growth factor (EGF); gelsolin (GSN); granzyme (GZM); haptoglobin (HP); heat shock protein 60 (HSP60); interleukin 6 (IL6); leptin (LEP); MF; matrix metalloproteinase-1 (MMP1); matrix metalloproteinase-3 (MMP3); matrix metalloproteinase-9 (MMP9); resistin (RETN); serum amyloid (SAA); tumor necrosis factor receptor, type 1 (TNF-R1); vascular cell adhesion molecule-1 (VCAM1); vascular endothelial growth factor A (VEGF-A); Calprotectin; intercellular adhesion molecule 1 (ICAM-1); interleukin-1 beta (IL-1B); interleukin-6 receptor (IL-6R); interleukin-8 (IL-8); interleukin-8 (IL-10); interleukin-8 (IL-17); interleukin-8 (IL-18); interleukin-8 (IL-21); L-selectin; MDC; P-selectin; pyridinoline (PYD); S100 A12; S100A14; TIMP metallopeptidase inhibitor 1 (TIMP1); TNF receptor-associated protein 1 (TRAP-1); transthyretin (TTR); tumor protein 53 (TP53); and YKL-40; determining whether the sample concentration for each said biomarker is statistically significantly greater than minimum diagnostic concentrations of corresponding control biomarkers that are indicative of JIA; and classifying disease activity of JIA in the subject, or predicting flare activity in the subject based at least in part on the determination of whether the sample concentrations for the biomarkers from the subject are statistically significantly greater than minimum diagnostic concentrations indicative of JIA. In an embodiment, the biomarkers comprise VCAM-1, EGF, VEGF-A, IL-6, TNF-R1, MMP-1, MMP-3, YKL-40, Leptin, Resistin, SAA, and CRP. In an embodiment, the biomarkers comprise IL-6, MMP3, CRP, TNF-R1, Calprotectin, YKL-40, ICAM-1, SAA, VCAM-1 and MMP1. In an embodiment, the biomarkers comprise IL-6, MMP3, CRP, TNF-R1, YKL-40, ICAM-1, SAA, VCAM-1 and MMP1. In an embodiment, the sample concentrations for the subject are predictive of a clinical assessment. In an embodiment, the clinical assessment is selected from the group consisting of physician global assessment of disease activity (MD global), parent/child global assessment of well-being (PGA), child/parent health assessment questionnaire (CHAQ), active arthritic joint counts, Westergren erythrocyte sedimentation rate (ESR), and juvenile arthritis disease activity score (JADAS). In an embodiment, the JIA is JIA is selected from the group consisting of oligoarticular JIA, polyarticular rheumatoid factor (RF) positive JIA, polyarticular RF negative JIA, systemic JIA, psoriatic JIA, enthesitis-related arthritis, and undifferentiated arthritis. In an embodiment, the subject has received a treatment for JIA, and determining efficacy of the treatment based on a statistically significant difference between the sample concentrations from the subject and the sample concentrations of the control. In an embodiment, a report is prepared in a format that is capable of being disseminated to the subject or a caregiver of the subject that provides information allowing the subject or caregiver to make decisions based on the disease or flare activity.

In another embodiment of the invention, a method for monitoring the presence or absence of juvenile idiopathic arthritis (JIA) disease activity in a subject, or for predicting flare activity in a subject having JIA is provided. The method comprises determining a first dataset associated with samples from a population of individuals wherein said population is negative for JIA, wherein said first dataset comprises quantitative data for three or more biomarkers selected from the group consisting of alpha-2-macroglobulin (A2M); amyloid P component, serum (SAP); angiopoietin 1 (AGP1) antithrombin III (ATIII); ataxia telangiectasia mutated (ATM); B-cell activating factor (BAFF); chemokine (C-C motif) ligand 2 (CCL2); chemokine (C-C motif) ligand 3 (CCL3); chemokine (C-C motif) ligand 11 (CCL11); chemokine (C-C motif) ligand 22 (CCL22); chemokine (C-X-C motif) ligand 9 (CXCL9); chemokine (C-X-C motif) ligand 10 (CXCL10); CD40 ligand (CD40LG); C-reactive protein (CRP); complement C3; complement C4; complement factor H (CFH); epidermal growth factor (EGF); gelsolin (GSN); granzyme (GZM); haptoglobin (HP); heat shock protein 60 (HSP60); interleukin 6 (IL6); leptin (LEP); MF; matrix metalloproteinase-1 (MMP1); matrix metalloproteinase-3 (MMP3); matrix metalloproteinase-9 (MMP9); resistin (RETN); serum amyloid (SAA); tumor necrosis factor receptor, type 1 (TNF-R1); vascular cell adhesion molecule-1 (VCAM1); vascular endothelial growth factor A (VEGF-A); YKL-40; Calprotectin; intercellular adhesion molecule 1 (ICAM-1); interleukin-1 beta (IL-1B); interleukin-6 receptor (IL-6R); interleukin-8 (IL-8); interleukin-8 (IL-10); interleukin-8 (IL-17); interleukin-8 (IL-18); interleukin-8 (IL-21); L-selectin; MDC; P-selectin; pyridinoline (PYD); S100 A12; S100A14; TIMP metallopeptidase inhibitor 1 (TIMP1); TNF receptor-associated protein 1 (TRAP-1); transthyretin (TTR); tumor protein 53 (TP53); and YKL-40; determining a plurality of DAI scores for the individuals in said population based on the first dataset; deriving an aggregate DAI value for said population; determining a second dataset associated with a sample from said subject wherein said second dataset comprises the selected biomarkers; determining a DAI score for said subject; comparing the aggregate DAI value to the DAI score for the subject; and determining disease activity of JIA in the subject, or predicting flare activity in the subject based at least in part on said comparison. In an embodiment, the biomarkers comprise VCAM-1, EGF, VEGF-A, IL-6, TNF-R1, MMP-1, MMP-3, YKL-40, Leptin, Resistin, SAA, and CRP. In an embodiment, the biomarkers comprise IL-6, MMP3, CRP, TNF-R1, Calprotectin, YKL-40, ICAM-1, SAA, VCAM-1 and MMP1. In an embodiment, the biomarkers comprise IL-6, MMP3, CRP, TNF-R1, YKL-40, ICAM-1, SAA, VCAM-1 and MMP1. In an embodiment, the datasets are obtained by a method comprising obtaining said samples from said population and said sample from said subject, wherein said samples comprise a plurality of analytes; contacting said samples with reagents; generating a plurality of complexes between said reagents with said plurality of analytes; and detecting said plurality of complexes to obtain said datasets wherein said datasets comprise quantitative data for said biomarkers. In an embodiment, the DAI score for the subject is predictive of a clinical assessment. In an embodiment, said clinical assessment is selected from the group consisting of physician global assessment of disease activity (MD global), parent/child global assessment of well-being (PGA), child/parent health assessment questionnaire (CHAR), active arthritic joint counts, Westergren erythrocyte sedimentation rate (ESR), and juvenile arthritis disease activity score (JADAS). In an embodiment, said JIA is selected from the group consisting of oligoarticular JIA, polyarticular rheumatoid factor (RF) positive JIA, polyarticular RF negative JIA, systemic JIA, psoriatic JIA, enthesitis-related arthritis, and undifferentiated arthritis. In an embodiment, the method further comprises receiving a third dataset associated with a second sample obtained from said subject, wherein said sample obtained from said subject and said second sample are obtained from said subject at different times; determining a second DAI score for said subject from said third dataset; and comparing said DAI score and said second DAI score for said subject to determine a change in said DAI scores, wherein said change indicates a change in JIA activity in said subject, or the prediction of flare in a subject having JIA. In an embodiment, a report is prepared in a format that is capable of being disseminated to the subject or a caregiver of the subject that provides information allowing the subject or caregiver to make decisions based on the disease or flare activity. In an embodiment, wherein said subject has received a treatment for JIA, the method further comprises the steps of determining a second DAI score for a second subject wherein said second subject is of the same species as said first subject and wherein said second subject has received treatment for JIA; comparing said DAI score of said subject to said second DAI score; and determining a treatment efficacy for said first subject based on said score comparison.

In another embodiment of the invention, a computer-implemented method for generating quantitative data for a subject is provided. The method comprises performing at least one immunoassay on a first sample from the first subject to generate a first dataset comprising the quantitative data, wherein the quantitative data comprises at least three or more biomarkers selected from the group consisting of alpha-2-macroglobulin (A2M); amyloid P component, serum (SAP); angiopoietin 1 (AGP1) antithrombin III (ATIII); ataxia telangiectasia mutated (ATM); B-cell activating factor (BAFF); chemokine (C-C motif) ligand 2 (CCL2); chemokine (C-C motif) ligand 3 (CCL3); chemokine (C-C motif) ligand 11 (CCL11); chemokine (C-C motif) ligand 22 (CCL22); chemokine (C-X-C motif) ligand 9 (CXCL9); chemokine (C-X-C motif) ligand 10 (CXCL10); CD40 ligand (CD40LG); C-reactive protein (CRP); complement C3; complement C4; complement factor H (CFH); epidermal growth factor (EGF); gelsolin (GSN); granzyme (GZM); haptoglobin (HP); heat shock protein 60 (HSP60); interleukin 6 (IL6); leptin (LEP); MF; matrix metalloproteinase-1 (MMP1); matrix metalloproteinase-3 (MMP3); matrix metalloproteinase-9 (MMP9); resistin (RETN); serum amyloid (SAA); tumor necrosis factor receptor, type 1 (TNF-R1); vascular cell adhesion molecule-1 (VCAM1); vascular endothelial growth factor A (VEGF-A); YKL-40; Calprotectin; intercellular adhesion molecule 1 (ICAM-1); interleukin-1 beta (IL-1B); interleukin-6 receptor (IL-6R); interleukin-8 (IL-8); interleukin-8 (IL-10); interleukin-8 (IL-17); interleukin-8 (IL-18); interleukin-8 (IL-21); L-selectin; MDC; P-selectin; pyridinoline (PYD); S100 A12; S100A14; TIMP metallopeptidase inhibitor 1 (TIMP1); TNF receptor-associated protein 1 (TRAP-1); transthyretin (TTR); tumor protein 53 (TP53); and YKL-40; comparing the first dataset to a trained dataset representing the at least three or more biomarkers; and generating quantitative data that is derived from the difference between the first and trained datasets, wherein the first subject has JIA or is suspected of having JIA. In an embodiment, the biomarkers comprise VCAM-1, EGF, VEGF-A, IL-6, TNF-R1, MMP-1, MMP-3, YKL-40, Leptin, Resistin, SAA, and CRP. In an embodiment, the biomarkers comprise IL-6, MMP3, CRP, TNF-R1, Calprotectin, YKL-40, ICAM-1, SAA, VCAM-1 and MMP1. In an embodiment, the biomarkers comprise IL-6, MMP3, CRP, TNF-R1, YKL-40, ICAM-1, SAA, VCAM-1 and MMP1. In an embodiment, the DAI score for the subject is predictive of a clinical assessment. In an embodiment, the clinical assessment is selected from the group consisting of physician global assessment of disease activity (MD global), parent/child global assessment of well-being (PGA), child/parent health assessment questionnaire (CHAQ), active arthritic joint counts, Westergren erythrocyte sedimentation rate (ESR), and juvenile arthritis disease activity score (JADAS). In an embodiment, said JIA is selected from the group consisting of oligoarticular JIA, polyarticular rheumatoid factor (RF) positive JIA, polyarticular RF negative JIA, systemic JIA, psoriatic JIA, enthesitis-related arthritis, and undifferentiated arthritis. In an embodiment, a report is prepared in a format that is capable of being disseminated to the subject or a caregiver of the subject that provides information allowing the subject or caregiver to make decisions based on the disease or flare activity.

In another embodiment of the invention, a method of treating a subject is provided. The method comprises classifying disease activity of JIA in the subject, or predicting flare activity in the subject and selecting a JIA therapeutic regimen based on said DAI score. The presence or absence of JIA is determined by providing a test sample comprising a sample of bodily fluid taken from the mammal; determining sample concentrations for three or more biomarkers selected from the group consisting of alpha-2-macroglobulin (A2M); amyloid P component, serum (SAP); angiopoietin 1 (AGP1) antithrombin III (ATIII); ataxia telangiectasia mutated (ATM); B-cell activating factor (BAFF); chemokine (C-C motif) ligand 2 (CCL2); chemokine (C-C motif) ligand 3 (CCL3); chemokine (C-C motif) ligand 11 (CCL11); chemokine (C-C motif) ligand 22 (CCL22); chemokine (C-X-C motif) ligand 9 (CXCL9); chemokine (C-X-C motif) ligand 10 (CXCL10); CD40 ligand (CD40LG); C-reactive protein (CRP); complement C3; complement C4; complement factor H (CFH); epidermal growth factor (EGF); gelsolin (GSN); granzyme (GZM); haptoglobin (HP); heat shock protein 60 (HSP60); interleukin 6 (IL6); leptin (LEP); MF; matrix metalloproteinase-1 (MMP1); matrix metalloproteinase-3 (MMP3); matrix metalloproteinase-9 (MMP9); resistin (RETN); serum amyloid (SAA); tumor necrosis factor receptor, type 1 (TNF-R1); vascular cell adhesion molecule-1 (VCAM1); vascular endothelial growth factor A (VEGF-A); Calprotectin; intercellular adhesion molecule 1 (ICAM-1); interleukin-1 beta (IL-1B); interleukin-6 receptor (IL-6R); interleukin-8 (IL-8); interleukin-8 (IL-10); interleukin-8 (IL-17); interleukin-8 (IL-18); interleukin-8 (IL-21); L-selectin; MDC; P-selectin; pyridinoline (PYD); S100 A12; S100A14; TIMP metallopeptidase inhibitor 1 (TIMP1); TNF receptor-associated protein 1 (TRAP-1); transthyretin (TTR); tumor protein 53 (TP53); and YKL-40; determining whether the sample concentration for each said biomarker is statistically significantly greater than minimum diagnostic concentrations of corresponding control biomarkers that are indicative of JIA; and classifying the subject as suffering from JIA based at least in part on the determination of whether the sample concentrations for the biomarkers from the subject are statistically significantly greater than minimum diagnostic concentrations indicative of JIA. In an embodiment, the JIA therapeutic regimen is provided. In an embodiment, a response to the treatment based on said DAI score is determined. In an embodiment a JIA treatment course based on said DAI score is determined.

BRIEF DESCRIPTION OF THE DRAWINGS

The skilled artisan will understand that the drawings, described below, are for illustration purposes only. The drawings are not intended to limit the scope of the present teachings in any way.

FIG. 3 illustrates individual and VECTRA™ DA MBDA biomarker comparisons with JADAS and JADAS components based on Pearson Correlation Coefficients.

DESCRIPTION OF VARIOUS EMBODIMENTS

Figure 1A:
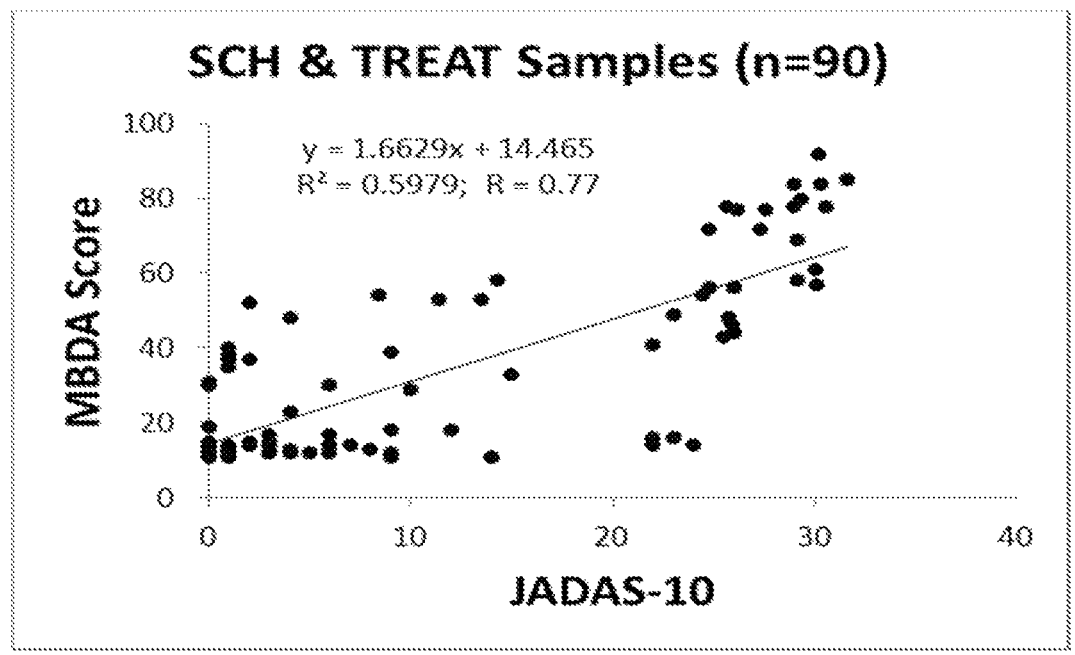
FIG. 1A illustrates the 12 biomarker VECTRA™ DA panel MBDA comparisons with JADAS.
Figure 1B:
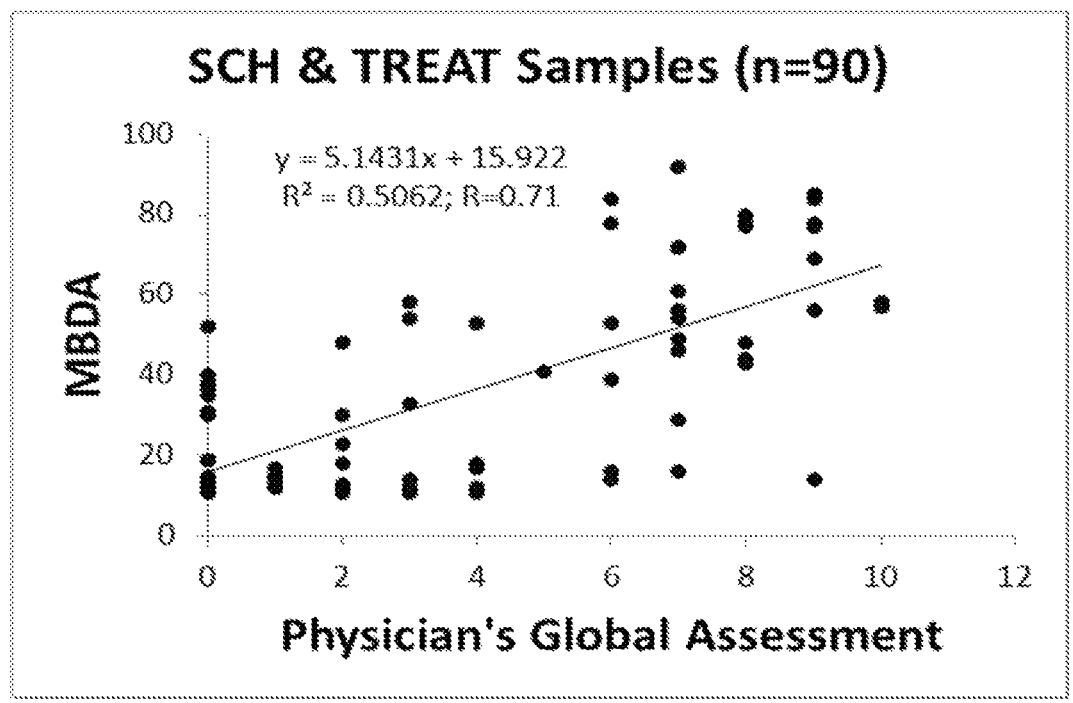
FIG. 1B illustrates the 12 biomarker VECTRA™ DA panel MBDA comparisons with Physician's Global Assessment.
Figure 1C:
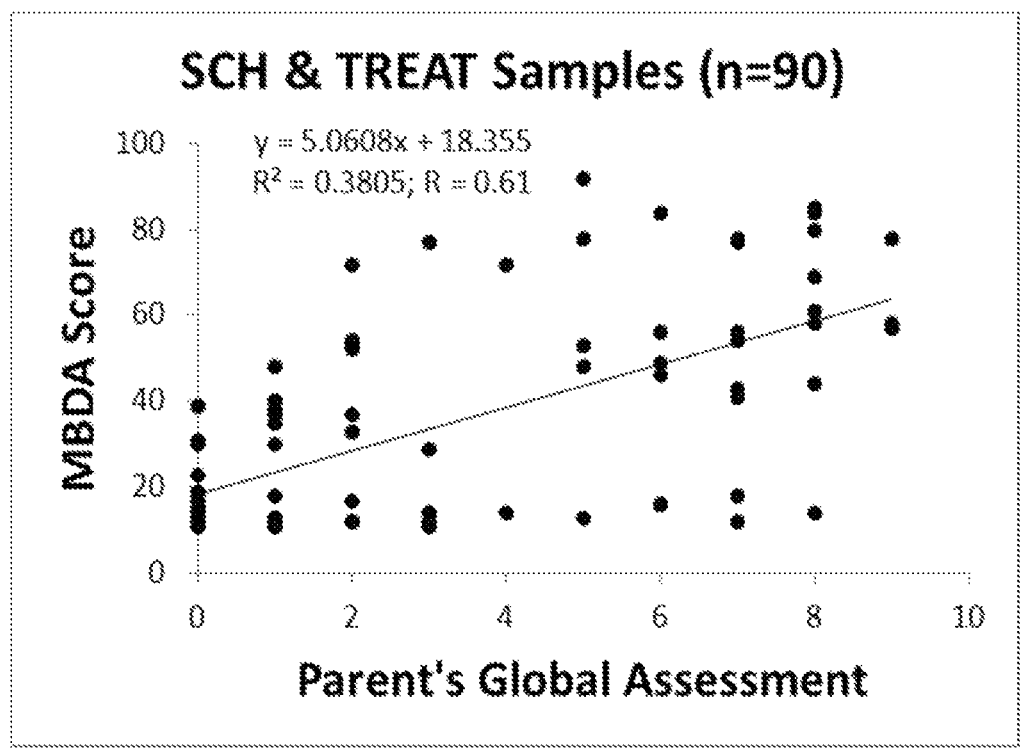
FIG. 1C illustrates the 12 biomarker VECTRA™ DA panel MBDA comparisons Parent's Global Assessment.
Figure 1D:
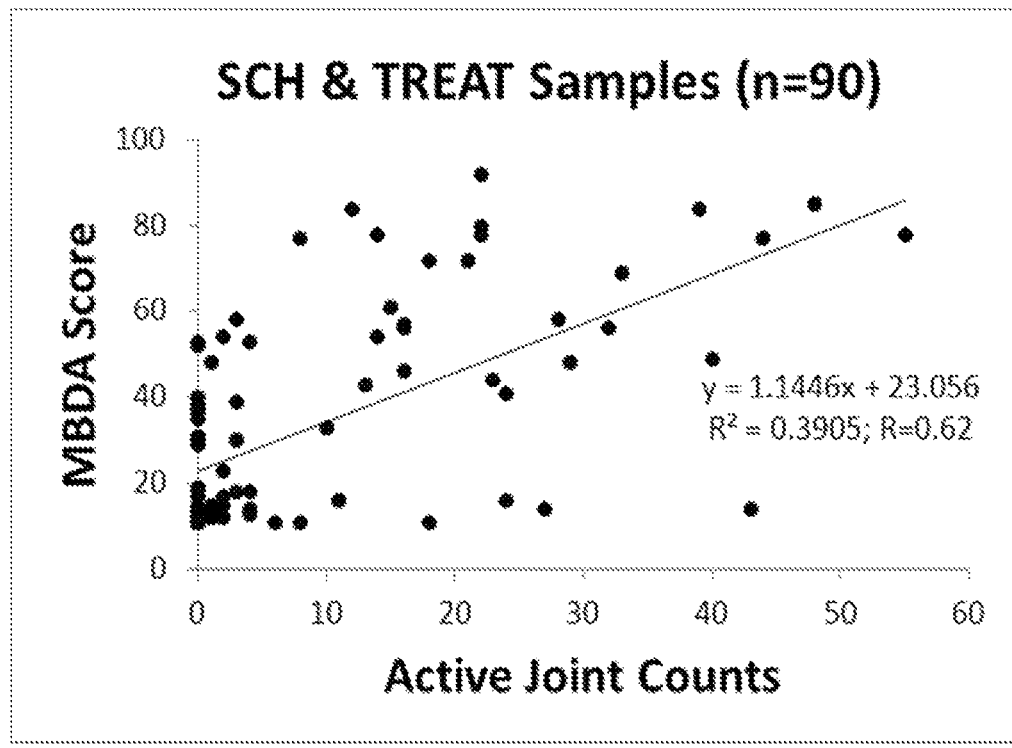
FIG. 1D illustrates the 12 biomarker VECTRA™ DA panel MBDA comparisons with Active Joint Counts.
Figure 2A:
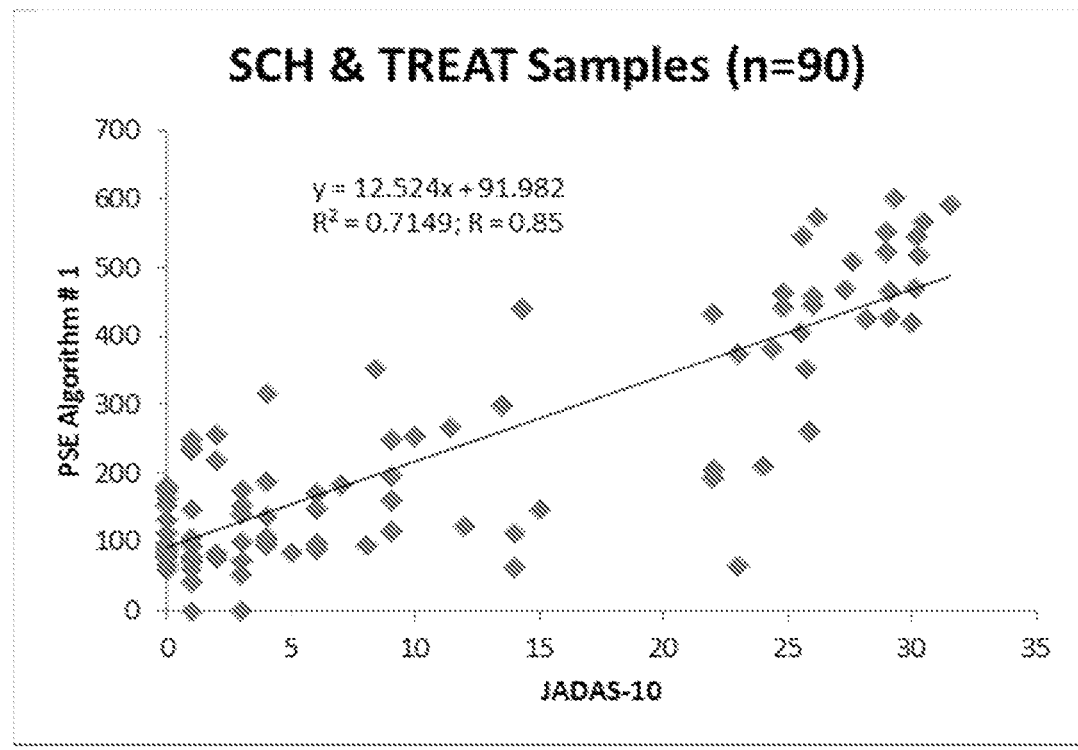
FIG. 2A illustrates a 9 or 10 biomarker panel comprising IL-6, MMP3, CRP, TNF-R1, with or w/o Calprotectin, YKL-40, ICAM-1, SAA, VCAM-1 and MMP1 compared with JADAS.
Figure 2B:
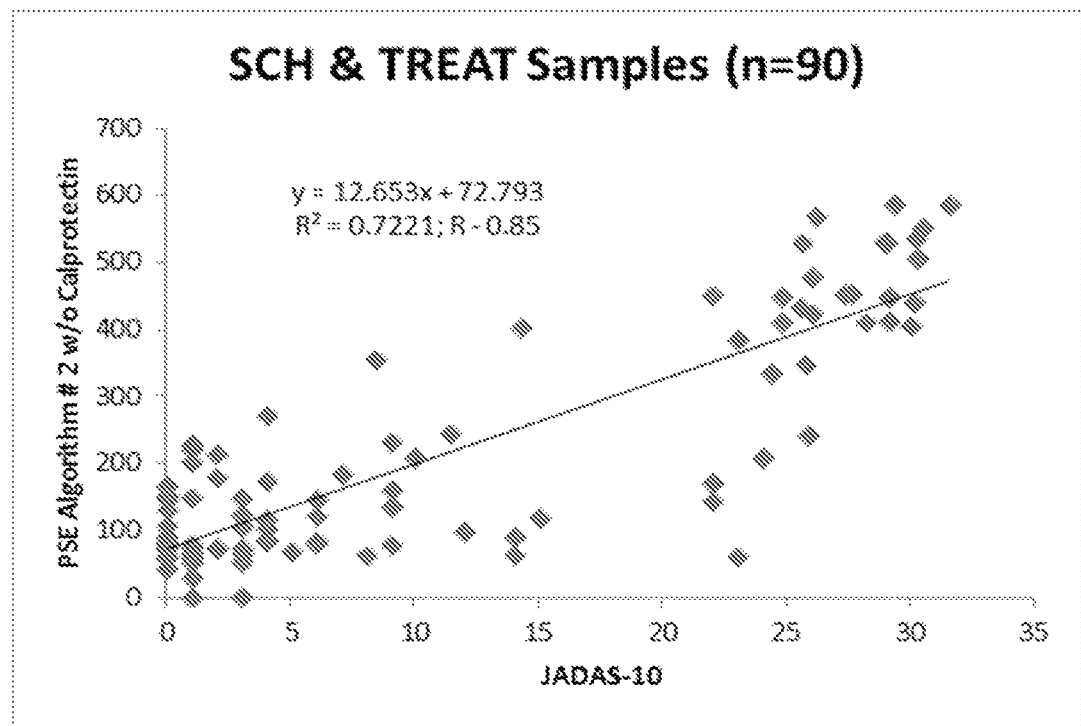
FIG. 2B illustrates a 9 or 10 biomarker panel comprising IL-6, MMP3, CRP, TNF-R1, with or w/o Calprotectin, YKL-40, ICAM-1, SAA, VCAM-1 and MMP1 compared with JADAS without Calprotectin.
Figure 2C:
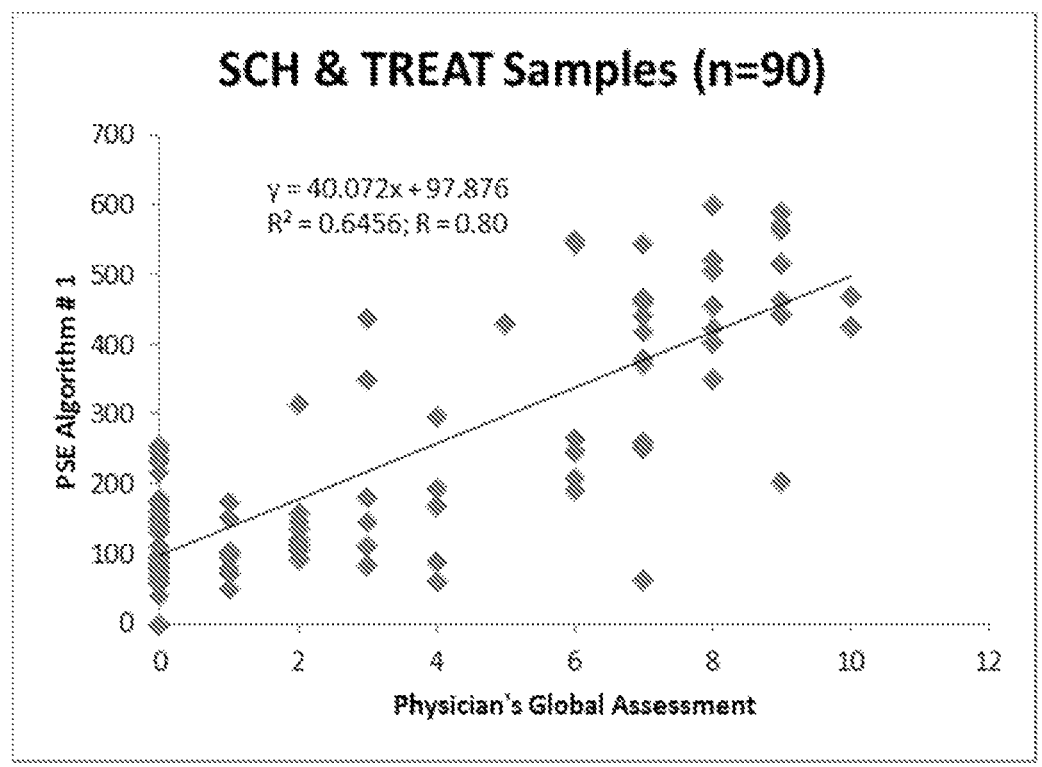
FIG. 2C illustrates a 9 or 10 biomarker panel comprising IL-6, MMP3, CRP, TNF-R1, with or w/o Calprotectin, YKL-40, ICAM-1, SAA, VCAM-1 and MMP1 compared with Physician's Global Assessment.
Figure 2D:
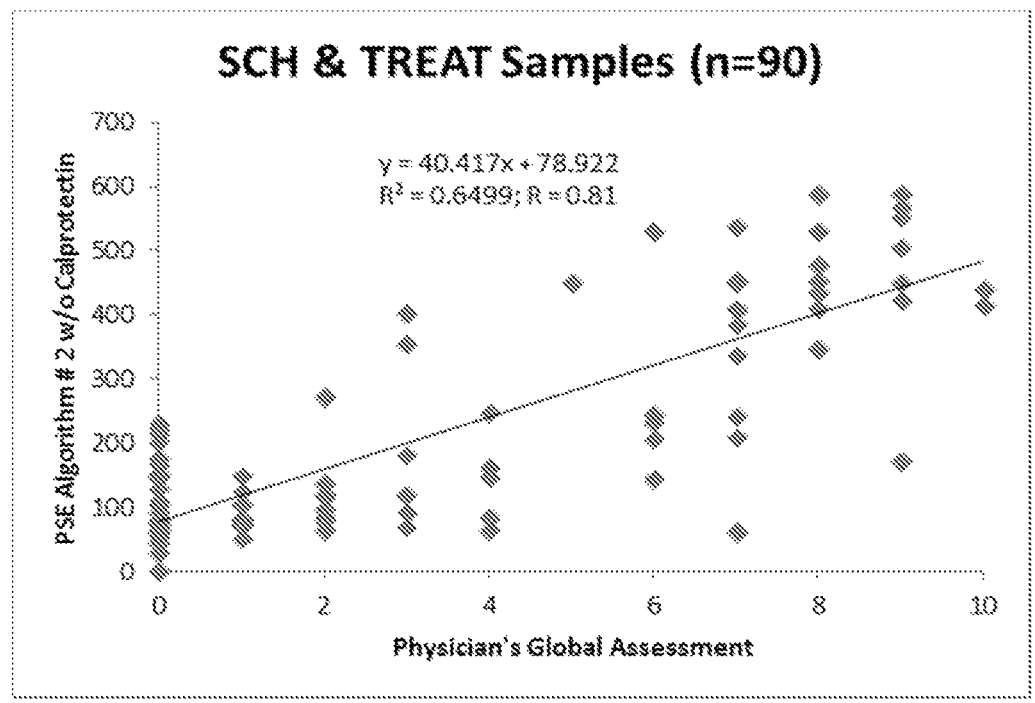
FIG. 2D illustrates a 9 or 10 biomarker panel comprising IL-6, MMP3, CRP, TNF-R1, with or w/o Calprotectin, YKL-40, ICAM-1, SAA, VCAM-1 and MMP1 compared with Physician's Global Assessment without Calprotectin.

These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The present teachings relate generally to diagnostic applications of biomarkers associated with subjects having inflammatory and/or autoimmune diseases, such as for example JIA, and that are useful in determining or assessing disease or flare activity.

Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control. It must be noted that, as used in the specification and the appended claims, the singular forms "a," "an," and "the" include plural referents unless the context clearly dictates otherwise.

Definitions

"Accuracy" refers to the degree that a measured or calculated value conforms to its actual value. "Accuracy" in clinical testing relates to the proportion of actual outcomes (true positives or true negatives, wherein a subject is correctly classified as having disease or as healthy/normal, respectively) versus incorrectly classified outcomes (false positives or false negatives, wherein a subject is incorrectly classified as having disease or as healthy/normal, respectively). Other terms related to "accuracy" (some being examples of measures of accuracy) can include, for example, "sensitivity," "specificity," "positive predictive value (PPV)," "the AUC," "negative predictive value (NPV)," "likelihood," and "odds ratio." "Analytical accuracy," in the context of the present teachings, refers to the repeatability and predictability of the measurement process. Analytical accuracy can be summarized in such measurements as, e.g., coefficients of variation (CV), and tests of concordance and calibration of the same samples or controls at different times or with different assessors, users, equipment, and/or reagents. See, e.g., R. Vasan, *Circulation* 2006, 113(19):2335-2362 for a summary of considerations in evaluating new biomarkers.

The term "algorithm" encompasses any formula, model, mathematical equation, algorithmic, analytical or programmed process, or statistical technique or classification analysis that takes one or more inputs or parameters, whether continuous or categorical, and produces an output value, index, index value or score. Examples of algorithms include but are not limited to ratios, sums, regression operators such as exponents or coefficients, biomarker value transformations and normalizations (including, without limitation, normalization schemes that are based on clinical parameters such as age, gender, ethnicity, etc.), rules and guidelines, statistical classification models, and neural networks trained on populations. Also of use in the context of biomarkers are linear and non-linear equations and statistical classification analyses to determine the relationship between (a) levels of biomarkers detected in a subject sample and (b) the level of the respective subject's disease activity.

"ALLMRK" in the present teachings refers to a specific group, panel, or set of biomarkers, as the term "biomarkers" is defined herein. Where the biomarkers of certain embodiments of the present teachings are proteins, the gene symbols and names used herein are to be understood to refer to the protein products of these genes, and the protein products of these genes are intended to include any protein isoforms of these genes, whether or not such isoform sequences are specifically described herein. Where the biomarkers are nucleic acids, the gene symbols and names used herein are to refer to the nucleic acids (DNA or RNA) of these genes, and the nucleic acids of these genes are intended to include any transcript variants of these genes, whether or not such transcript variants are specifically described herein. The ALLMRK group of the present teachings is the group of markers consisting of the following, where the name(s) or symbols in parentheses at the end of the marker name generally refers to the gene name, if known, or an alias: adiponectin, C1Q and collagen domain containing (ADIPOQ); alpha-2-macroglobulin (A2M); adrenomedullin (ADM); alkaline phosphatase, liver/bone/kidney (ALPL); amyloid P component, serum (APCS or SAP); angiopoietin 1 (AGP1); antithrombin III (ATIII); advanced glycosylation end product-specific receptor (AGER); apolipoprotein A-I (APOA1); apolipoprotein A-II (APOA2); apolipoprotein B (including Ag(x) antigen) (APOB); apolipoprotein C-II (APOC2); apolipoprotein C-III (APOC3); apolipoprotein E (APOE); bone gamma-carboxyglutamate (gla) protein (BGLAP, or osteocalcin); ataxia telangiectasia mutated (ATM); B-cell activating factor (BAFF); bone morphogenetic protein 6 (BMP6); calcitonin-related polypeptide beta (CALCB); calprotectin (dimer of S100A8 and S100A9 protein subunits); chemokine (C-C motif) ligand 2 (CCL2); chemokine (C-C motif) ligand 3 (CCL3); chemokine (C-C motif) ligand 5 (CCL5); chemokine (C-C motif) ligand 11 (CCL11); chemokine (C-C motif) ligand 22 (CCL22); chemokine (C-X-C motif) ligand 9 (CXCL9); chemokine (C-X-C motif) ligand 10 (CXCL10); CD40 ligand (CD40LG); chitinase 3-like 1 (cartilage glycoprotein-39) (CHI3L1, or YKL-40); cartilage oligomeric matrix protein (COMP); C-reactive protein, pentraxin-related (CRP); CS3B3 epitope, a cartilage fragment; colony stimulating factor 1 (macrophage) (CSF1, or MCSF); colony stimulating factor 2 (granulocyte-macrophage) (CSF2); colony stimulating factor 3 (granulocyte) (CSF3); complement C3; complement C4; complement factor H (CFH); cystatin C (CST3); endoplasmic reticulum aminopeptidase 1 (ERAP1); epidermal growth factor (beta-urogastrone) (EGF); epidermal growth factor receptor (erythroblastic leukemia viral (v-erb-b) oncogene homolog, avian) (EGFR); erythropoietin (EPO); Fas (TNF receptor superfamily, member 6) (FAS); fibrinogen alpha chain (FGA); fibroblast growth factor 2 (basic) (FGF2); fibrinogen; fms-related tyrosine kinase 1 (vascular endothelial growth factor/vascular permeability factor receptor) (FLT1); fms-related tyrosine kinase 3 ligand (FLT3LG); fms-related tyrosine kinase 4 (FLT4); follicle stimulating hormone; follicle stimulating hormone, beta polypeptide (FSHB); follastatin-like protein 1 (FSTL-1); gastric inhibitory polypeptide (GIP); ghrelin; ghrelin/obestatin prepropeptide (GHRL); gelsolin (GSN); granzyme (GZM); growth hormone 1 (GH1); GLP1; hepatocyte growth factor (HGF); haptoglobin (HP); heat shock protein 60 (HSP60); intercellular adhesion molecule 1 (ICAM1); intercellular adhesion molecule 3 (ICAM3); ICTP; interferon, alpha 1 (IFNA1); interferon, alpha 2 (IFNA2); glial cell derived neurotrophic factor (GDNF); interferon, gamma (IFNG); insulin-like growth factor binding protein 1 (IGFBP1); interleukin 6 (IL6); interleukin 10 (IL10); interleukin 12; interleukin 12A (natural killer cell stimulatory factor 1, cytotoxic lymphocyte maturation factor 1, p35) (IL12A); interleukin 12B (natural killer cell stimulatory factor 2, cytotoxic lymphocyte maturation factor 2, p40) (IL12B); interleukin 13 (IL13); interleukin 15 (IL15); interleukin 17 (IL-17); interleukin 17A (IL17A); interleukin 18 (interferon-gamma-inducing factor) (IL18); interleukin 21 (IL-21); interleukin 1, alpha (ILIA); interleukin 1, beta (IL1B); interleukin 1 receptor, type I (IL1R1); interleukin 1 receptor, type II (IL1R2); interleukin 1 receptor antagonist (IL1RN, or IL1RA); interleukin 2 (IL2); interleukin 2 receptor; interleukin 2 receptor, alpha (IL2RA); interleukin 3 (colony-stimulating factor, multiple) (IL3); interleukin 4 (IL4); interleukin 4 receptor (IL4R); interleukin 5 (colony-stimulating factor, eosinophil) (IL5); interleukin 6 (interferon, beta 2) (IL6); interleukin 6 receptor (IL6R); interleukin 6 signal transducer (gp130, oncostatin M receptor) (IL6ST); interleukin 7 (IL7); interleukin 8 (IL8); insulin (INS); interleukin 9 (IL9); L-selectin; kinase insert domain receptor (a type III receptor tyrosine kinase) (KDR); v-kit Hardy-Zuckerman 4 feline sarcoma viral oncogene homolog (KIT); keratan sulfate, or KS; leptin (LEP); leukemia inhibitory factor (cholinergic differentiation factor) (LIF); lymphotoxin alpha (TNF superfamily, member 1) (LTA); lysozyme (renal amyloidosis) (LYZ); MDC; MF; matrix metallopeptidase 1 (interstitial collagenase) (MMP1); matrix metallopeptidase 3 (interstitial collagenase) (MMP3); matrix metallopeptidase 9 (interstitial collagenase) (MMP9); matrix metallopeptidase 10 (stromelysin 2) (MMP10); matrix metallopeptidase 2 (gelatinase A, 72 kDa gelatinase, 72 kDa type IV collagenase) (MMP2); matrix metallopeptidase 3 (stromelysin 1, progelatinase) (MMP3); matrix metallopeptidase 9 (gelatinase B, 92 kDa gelatinase, 92 kDa type IV collagenase) (MMP9); monocyte chemotactic protein 1 (MCP-1); macrophage inhibitory factor (MIF); myeloperoxidase (MPO); nerve growth factor (beta polypeptide) (NGF); natriuretic peptide precursor B (NPPB, or NT-proBNP); neurotrophin 4 (NTF4); osteoprotegerin (OPG); P-selectin; platelet-derived growth factor alpha polypeptide (PDGFA); the dimer of two PDGFA subunits (or PDGF-AA); the dimer of one PDGFA subunit and one PDGFB subunit (or PDGF-AB); platelet-derived growth factor beta polypeptide (PDGFB); prostaglandin E2 (PGE2); phosphatidylinositol glycan anchor biosynthesis, class F (PIGF); proopiomelanocortin (POMC); pancreatic polypeptide (PPY); prolactin (PRL); pentaxin-related gene, rantes; rapidly induced by IL-1 beta (PTX3, or pentraxin 3); pyridinoline (PYD); peptide YY (PYY); receptor activator of NF-κβ (RANKL); resistin (RETN); serum amyloid A1 (SAA1); selectin E (SELE); selectin L (SELL); selectin P (granule membrane protein 140 kDa, antigen CD62) (SELP); serpin peptidase inhibitor, clade E (nexin, plasminogen activator inhibitor type 1), member 1 (SERPINE1); secretory leukocyte peptidase inhibitor (SLPI); sclerostin (SOST); secreted protein, acidic, cysteine-rich (SPARC, or osteonectin); secreted phosphoprotein 1 (SPP1, or osteopontin); TIMP metallopeptidase inhibitor 1 (TIMP1); transforming growth factor, alpha (TGFA); thrombomodulin (THBD); TNF receptor-associated protein 1 (TRAP-1); transthyretin (TTR); tumor necrosis factor (TNF superfamily, member 2; or TNF-alpha) (TNF); tumor necrosis factor receptor superfamily, member 11b (TNFRSF11B, or osteoprotegerin); tumor necrosis factor receptor superfamily, member 1A (TNFRSF1A or TNF-R1); tumor necrosis factor receptor superfamily, member 1B (TNFRSF1B); tumor necrosis factor receptor superfamily, member 8 (TNFRSF8); tumor necrosis factor receptor superfamily, member 9 (TNFRSF9); tumor necrosis factor (ligand) superfamily, member 11 (TNFSF11, or RANKL); tumor necrosis factor (ligand) superfamily, member 12 (TNFSF12, or TWEAK); tumor necrosis factor (ligand) superfamily, member 13 (TNFSF13, or APRIL); tumor necrosis factor (ligand) superfamily, member 13b (TNFSF13B, or BAFF); tumor protein 53 (TP53); tumor necrosis factor (ligand) superfamily, member 14 (TNFSF14, or LIGHT); tumor necrosis factor (ligand) superfamily, member 18 (TNFSF18); thyroid peroxidase (TPO); vascular cell adhesion molecule 1 (VCAM1); vascular endothelial growth factor A (VEGFA); and YKL-40.

The term "analyte" in the context of the present teachings can mean any substance to be measured, and can encompass biomarkers, markers, nucleic acids, electrolytes, metabolites, proteins, sugars, carbohydrates, fats, lipids, cytokines, chemokines, growth factors, proteins, peptides, nucleic acids, oligonucleotides, metabolites, mutations, variants, polymorphisms, modifications, fragments, subunits, degradation products and other elements. For simplicity, standard gene symbols may be used throughout to refer not only to genes but also gene products/proteins, rather than using the standard protein symbol; e.g., APOA1 as used herein can refer to the gene APOA1 and also the protein ApoAI. In general, hyphens are dropped from analyte names and symbols herein (IL-6=IL6).

To "analyze" includes determining a value or set of values associated with a sample by measurement of analyte levels in the sample. "Analyze" may further comprise comparing the levels against constituent levels in a sample or set of samples from the same subject or other subject(s). The biomarkers of the present teachings can be analyzed by any of various methods. Some such methods include but are not limited to: measuring serum protein or sugar or metabolite or other analyte level, measuring enzymatic activity, and measuring gene expression. Some such methods include analyzing a panel of biomarkers comprising at least some minimum number of test biomarkers disclosed herein as diagnostic, such test biomarkers optionally representing at least some minimum proportion of the total panel and/or contributing at least some minimum weight to the diagnostic test value/score derived from the measured levels of the panel.

The term "antibody" refers to any immunoglobulin-like molecule that reversibly binds to another with the required selectivity. Thus, the term includes any such molecule that is capable of selectively binding to a biomarker of the present teachings. The term includes an immunoglobulin molecule capable of binding an epitope present on an antigen. The term is intended to encompass not only intact immunoglobulin molecules, such as monoclonal and polyclonal antibodies, but also antibody isotypes, recombinant antibodies, bi-specific antibodies, humanized antibodies, chimeric antibodies, anti-idiopathic (anti-ID) antibodies, single-chain antibodies, Fab fragments, F(ab') fragments, fusion protein antibody fragments, immunoglobulin fragments, $F_v$ fragments, single chain $F_v$ fragments, and chimeras comprising an immunoglobulin sequence and any modifications of the foregoing that comprise an antigen recognition site of the required selectivity.

"Autoimmune disease" encompasses any disease, as defined herein, resulting from an immune response against substances and tissues normally present in the body. Examples of suspected or known autoimmune diseases include rheumatoid arthritis, juvenile idiopathic arthritis, seronegative spondyloarthropathies, ankylosing spondylitis, psoriatic arthritis, antiphospholipid antibody syndrome, autoimmune hepatitis, Behcet's disease, bullous pemphigoid, coeliac disease, Crohn's disease, dermatomyositis, Goodpasture's syndrome, Graves' disease, Hashimoto's disease, idiopathic thrombocytopenic purpura, IgA nephropathy, juvenile idiopathic arthritis, Kawasaki disease, systemic lupus erythematosus, mixed connective tissue disease, multiple sclerosis, myasthenia gravis, polymyositis, primary biliary cirrhosis, psoriasis, scleroderma, Sjögren's syndrome, ulcerative colitis, vasculitis, Wegener's granulomatosis, temporal arteritis, Takayasu's arteritis, Henoch-Schonlein purpura, leucocytoclastic vasculitis, polyarteritis nodosa, Churg-Strauss Syndrome, and mixed cryoglobulinemic vasculitis.

"Biomarker," "biomarkers," "marker" or "markers" in the context of the present teachings encompasses, without limitation, cytokines, chemokines, growth factors, proteins, peptides, nucleic acids, oligonucleotides, and metabolites, together with their related metabolites, mutations, isoforms, variants, polymorphisms, modifications, fragments, subunits, degradation products, elements, and other analytes or sample-derived measures. Biomarkers can also include mutated proteins, mutated nucleic acids, variations in copy numbers and/or transcript variants. Biomarkers also encompass non-blood borne factors and non-analyte physiological markers of health status, and/or other factors or markers not measured from samples (e.g., biological samples such as bodily fluids), such as clinical parameters and traditional factors for clinical assessments. Biomarkers can also include any indices that are calculated and/or created mathematically. Biomarkers can also include combinations of any one or more of the foregoing measurements, including temporal trends and differences.

A "clinical assessment," or "clinical datapoint" or "clinical endpoint," in the context of the present teachings can refer to a measure of disease activity or severity. A clinical assessment can include a score, a value, or a set of values that can be obtained from evaluation of a sample (or population of samples) from a subject or subjects under determined conditions. A clinical assessment can also be a questionnaire completed by a subject. A clinical assessment can also be predicted by biomarkers and/or other parameters. One of skill in the art will recognize that the clinical assessment for JIA, as an example, can comprise, without limitation, one or more of the following: physician global assessment of disease activity (MD global), parent/child global assessment of well-being (PGA), child/parent health assessment questionnaire (CHAD), active arthritic joint counts, Westergren erythrocyte sedimentation rate (ESR), and juvenile arthritis disease activity score (JADAS).

The term "clinical parameters" in the context of the present teachings encompasses all measures of the health status of a subject. A clinical parameter can be used to derive a clinical assessment of the subject's disease activity. Clinical parameters can include, without limitation: therapeutic regimen (including but not limited to therapies, whether conventional or biologics, steroids, etc.), TJC, SJC, morning stiffness, arthritis of three or more joint areas, arthritis of hand joints, symmetric arthritis, rheumatoid nodules, radiographic changes and other imaging, gender/sex, age, race/ethnicity, disease duration, diastolic and systolic blood pressure, resting heart rate, height, weight, body-mass index, family history, CCP status (i.e., whether subject is positive or negative for anti-CCP antibody), CCP titer, RF status, RF titer, ESR, CRP titer, menopausal status, and whether a smoker/non-smoker.

"Clinical assessment" and "clinical parameter" are not mutually exclusive terms. There may be overlap in members of the two categories. For example, CRP titer can be used as a clinical assessment of disease activity; or, it can be used as a measure of the health status of a subject, and thus serve as a clinical parameter.

Figure 10:
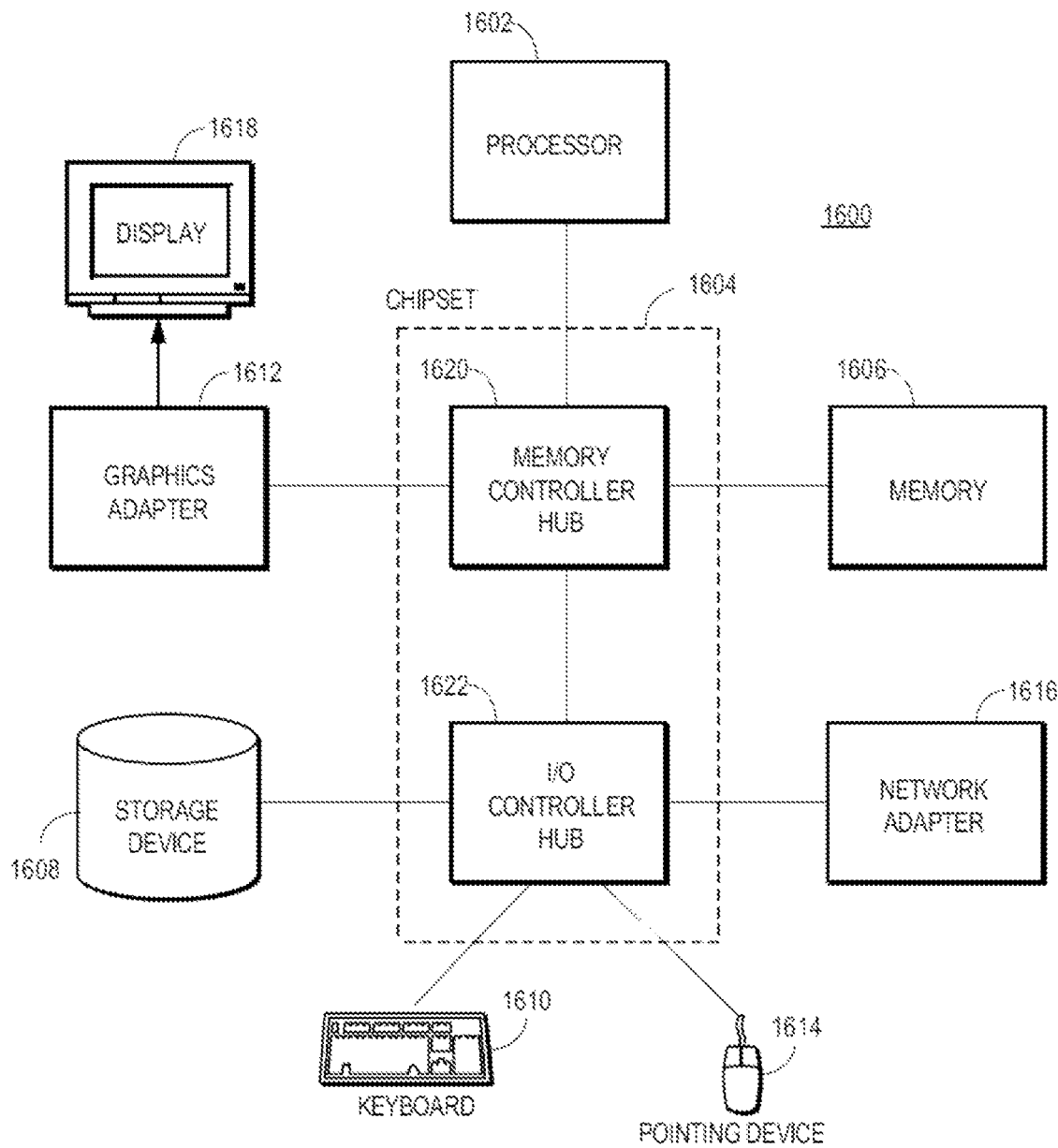
FIG. 10 is a high-level block diagram of a computer (1600). Illustrated are at least one processor (1602) coupled to a chipset (1604). Also coupled to the chipset (1604) are a memory (1606), a storage device (1608), a keyboard (1610), a graphics adapter (1612), a pointing device (1614), and a network adapter (1616). A display (1618) is coupled to the graphics adapter (1612). In one embodiment, the functionality of the chipset (1604) is provided by a memory controller hub 1620) and an I/O controller hub (1622). In another embodiment, the memory (1606) is coupled directly to the processor (1602) instead of the chipset (1604). The storage device 1608 is any device capable of holding data, like a hard drive, compact disk read-only memory (CD-ROM), DVD, or a solid-state memory device. The memory (1606) holds instructions and data used by the processor (1602). The pointing device (1614) may be a mouse, track ball, or other type of pointing device, and is used in combination with the keyboard (1610) to input data into the computer system (1600). The graphics adapter (1612) displays images and other information on the display (1618). The network adapter (1616) couples the computer system (1600) to a local or wide area network.

The term "computer" carries the meaning that is generally known in the art; that is, a machine for manipulating data according to a set of instructions. For illustration purposes only, FIG. 10 is a high-level block diagram of a computer (1600). A "computer" can have different and/or other components than those shown in FIG. 10. In addition, the computer 1600 can lack certain illustrated components. Moreover, the storage device (1608) can be local and/or remote from the computer (1600) (such as embodied within a storage area network (SAN)). A computer (1600) can be modified and adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device (1608), loaded into the memory (1606), and executed by the processor (1602). Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

The term "cytokine" in the present teachings refers to any substance secreted by specific cells of the immune system that carries signals locally between cells and thus has an effect on other cells. The term "cytokines" encompasses "growth factors." "Chemokines" are also cytokines. They are a subset of cytokines that are able to induce chemotaxis in cells; thus, they are also known as "chemotactic cytokines."

Calprotectin is a heteropolymer, comprising two protein subunits of gene symbols S100A8 and S100A9. ICTP is the carboxyterminal telopeptide region of type I collagen, and is liberated during the degradation of mature type I collagen. Type I collagen is present as fibers in tissue; in bone, the type I collagen molecules are cross-linked. The ICTP peptide is immunochemically intact in blood. (For the type I collagen gene, see official symbol COL1A1, HUGO Gene Nomenclature Committee; also known as 014; alpha 1 type I collagen; collagen alpha 1 chain type I; collagen of skin, tendon and bone, alpha-1 chain; and, pro-alpha-1 collagen type 1). Keratan sulfate (KS, or keratosulfate) is not the product of a discrete gene, but refers to any of several sulfated glycosaminoglycans. They are synthesized in the central nervous system, and are found especially in cartilage and bone. Keratan sulfates are large, highly hydrated molecules, which in joints can act as a cushion to absorb mechanical shock.

A "dataset" is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored.

In certain embodiments of the present teachings, a dataset of values is determined by measuring at least three biomarkers. This dataset is used by an interpretation function according to the present teachings to derive a DAI score (see definition, "DAI score," below), which provides a quantitative measure of inflammatory disease activity in a subject. In the context of JIA, the DAI score thus derived from this dataset is also useful in predicting a clinical assessment, with a high degree of association, as is shown in the Examples below.

The term "diagnosis" or "diagnosing" as used herein refers to methods by which a determination can be made as to whether an individual is likely to be suffering from a given disease or condition. The skilled artisan often makes a diagnosis on the basis of one or more diagnostic indicators, e.g., a biomarker, the presence, absence, amount, or change in amount of which is indicative of the presence, severity, or absence of the condition. Other diagnostic indicators can include patient history; physical symptoms, e.g., unexplained weight loss, fever, fatigue, pains, or skin anomalies; phenotype; genotype; or environmental or heredity factors. A diagnosis of a JIA is based on the evaluation of the one or more diagnostic indicators that is indicative of JIA. Each factor or symptom that is considered to be indicative for a diagnosis of JIA does not need to be exclusively related to the disease; e.g., there may be differential diagnoses that can be inferred from a diagnostic factor or symptom. Similarly, there may be instances where a factor or symptom that is indicative of JIA is present in an individual that does not have JIA. The term "diagnosis" does not refer to the ability to predict the development of a condition with 100% accuracy, or even that the development of the condition is more likely to occur than not. Instead, the skilled artisan will understand that the term "diagnosis" refers to an increased probability that certain course or outcome will occur; that is, that a course or outcome is more likely to occur in a patient exhibiting a given characteristic, e.g., the presence or level of a diagnostic indicator, when compared to individuals not exhibiting the characteristic. Diagnostic methods can be used independently, or in combination with other diagnosing methods known in the art to determine whether a course or outcome is more likely to occur in a patient exhibiting a given characteristic. The term "monitor" or "monitoring" carries its common usage, and can refer to, inter alia, the observation of disease commencement or progression.

The term "disease" in the context of the present teachings encompasses any disorder, condition, sickness, ailment, etc. that manifests in, e.g., a disordered or incorrectly functioning organ, part, structure, or system of the body, and results from, e.g., genetic or developmental errors, infection, poisons, nutritional deficiency or imbalance, toxicity, or unfavorable environmental factors.

A "disease activity index score," "DAI score," or simply "DAI," in the context of the present teachings, is a score that provides a quantitative measure of inflammatory disease activity or the state of inflammatory disease in a subject. Thus, "disease activity" as used herein is a measure of inflammatory disease activity or the state in inflammatory disease in a subject set of data from particularly selected biomarkers, e.g., markers selected from the ALLMRK set, can be input into an interpretation function according to the present teachings to derive the DAI score. The interpretation function, in some embodiments, can be created from predictive or multivariate modeling based on statistical algorithms. Input to the interpretation function can comprise the results of testing three or more of the ALLMRK set of biomarkers, alone or in combination with clinical parameters and/or clinical assessments, also described herein. In some embodiments of the present teachings, the DAI score is a quantitative measure of autoimmune disease activity. In some embodiments, the DAI score is a quantitative measure of JIA disease activity.

The term "flare activity" as used herein refers to an increase in a subject's disease activity or symptoms. Symptoms may include, but are not limited to, joint discomfort with or without swelling, joint pain, or joint stiffness.

"Inflammatory disease" in the context of the present teachings encompasses, without limitation, any disease, as defined herein, resulting from the biological response of vascular tissues to harmful stimuli, including but not limited to such stimuli as pathogens, damaged cells, irritants, antigens and, in the case of autoimmune disease, substances and tissues normally present in the body. Examples of inflammatory disease include JIA, RA, atherosclerosis, asthma, autoimmune diseases, chronic inflammation, chronic prostatitis, glomerulonephritis, hypersensitivities, inflammatory bowel diseases, pelvic inflammatory disease, reperfusion injury, transplant rejection, and vasculitis.

"Interpretation function," as used herein, means the transformation of a set of observed data into a meaningful determination of particular interest; e.g., an interpretation function may be a predictive model that is created by utilizing one or more statistical algorithms to transform a dataset of observed biomarker data into a meaningful determination of disease activity or the disease state of a subject.

A "minimum diagnostic concentration" is the concentration of an analyte or panel of analytes that defines the limit between the concentration range corresponding to normal disease-free function and the concentration reflective of an immune disorder.

"Measuring" or "measurement" or "detecting" in the context of the present teachings refers to determining the presence, absence, quantity, amount, or effective amount of a substance in a clinical or subject-derived sample, including the concentration levels of such substances, or evaluating the values or categorization of a subject's clinical parameters.

"Performance" in the context of the present teachings relates to the quality and overall usefulness of, e.g., a model, algorithm, or diagnostic or prognostic test. Factors to be considered in model or test performance include, but are not limited to, the clinical and analytical accuracy of the test, use characteristics such as stability of reagents and various components, ease of use of the model or test, health or economic value, and relative costs of various reagents and components of the test.

A "population" is any grouping of subjects of like specified characteristics. The grouping could be according to, for example but without limitation, clinical parameters, clinical assessments, therapeutic regimen, disease status (e.g. with disease or healthy), level of disease activity, etc. In the context of using the DAI score in comparing disease activity between populations, an aggregate value can be determined based on the observed DAI scores of the subjects of a population; e.g., at particular timepoints in a longitudinal study. The aggregate value can be based on, e.g., any mathematical or statistical formula useful and known in the art for arriving at a meaningful aggregate value from a collection of individual datapoints; e.g., mean, median, median of the mean, etc.

A "predictive model," which term may be used synonymously herein with "multivariate model" or simply a "model," is a mathematical construct developed using a statistical algorithm or algorithms for classifying sets of data. The term "predicting" refers to generating a value for a datapoint without actually performing the clinical diagnostic procedures normally or otherwise required to produce that datapoint; "predicting" as used in this modeling context should not be understood solely to refer to the power of a model to predict a particular outcome. Predictive models can provide an interpretation function; e.g., a predictive model can be created by utilizing one or more statistical algorithms or methods to transform a dataset of observed data into a meaningful determination of disease activity or the disease state of a subject. See Calculation of the DAI score for some examples of statistical tools useful in model development.

A "prognosis" is a prediction as to the likely outcome of a disease. Prognostic estimates are useful in, e.g., determining an appropriate therapeutic regimen for a subject.

A "quantitative dataset," as used in the present teachings, refers to the data derived from, e.g., detection and composite measurements of a plurality of biomarkers (i.e., two or more) in a subject sample. The quantitative dataset can be used in the identification, monitoring and treatment of disease states, and in characterizing the biological condition of a subject. It is possible that different biomarkers will be detected depending on the disease state or physiological condition of interest.

A "report," as used herein, refers to any written or electronic form of data, whether or not displayed, either in raw data form or analyzed as to its significance, including charts, graphs, plots, tables, or summary information manifesting the significance of the data as applied to a given medical or medical-related test.

A "sample" in the context of the present teachings refers to any biological sample that is isolated from a subject. A sample can include, without limitation, a single cell or multiple cells, fragments of cells, an aliquot of body fluid, whole blood, platelets, serum, plasma, red blood cells, white blood cells or leucocytes, endothelial cells, tissue biopsies, synovial fluid, lymphatic fluid, ascites fluid, and interstitial or extracellular fluid. The term "sample" also encompasses the fluid in spaces between cells, including gingival crevicular fluid, bone marrow, cerebrospinal fluid (CSF), saliva, mucous, sputum, semen, sweat, urine, or any other bodily fluids. "Blood sample" can refer to whole blood or any fraction thereof, including blood cells, red blood cells, white blood cells or leucocytes, platelets, serum and plasma. Samples can be obtained from a subject by means including but not limited to venipuncture, excretion, ejaculation, massage, biopsy, needle aspirate, lavage, scraping, surgical incision, or intervention or other means known in the art.

A "score" is a value or set of values selected so as to provide a quantitative measure of a variable or characteristic of a subject's condition, and/or to discriminate, differentiate or otherwise characterize a subject's condition. The value(s) comprising the score can be based on, for example, a measured amount of one or more sample constituents obtained from the subject, or from clinical parameters, or from clinical assessments, or any combination thereof. In certain embodiments the score can be derived from a single constituent, parameter or assessment, while in other embodiments the score can be derived from multiple constituents, parameters and/or assessments. The score can be based upon or derived from an interpretation function; e.g., an interpretation function derived from a particular predictive model using any of various statistical algorithms known in the art. A "change in score" can refer to the absolute change in score, e.g. from one timepoint to the next, or the percent change in score, or the change in the score per unit time (e.g., the rate of score change).

"Statistically significant" in the context of the present teachings means an observed alteration is greater than what would be expected to occur by chance alone (e.g., a "false positive"). Statistical significance can be determined by any of various methods well-known in the art. An example of a commonly used measure of statistical significance is the p-value. The p-value represents the probability of obtaining a given result equivalent to a particular datapoint, where the datapoint is the result of random chance alone. A result is often considered highly significant (not random chance) at a p-value less than or equal to 0.05.

A "subject" in the context of the present teachings is generally a mammal. The subject can be a patient. The term "mammal" as used herein includes but is not limited to a human, non-human primate, dog, cat, mouse, rat, cow, horse, and pig. Mammals other than humans can be advantageously used as subjects that represent animal models of inflammation. A subject can be male or female. A subject can be one who has been previously diagnosed or identified as having an inflammatory disease. A subject can be one who has already undergone, or is undergoing, a therapeutic intervention for an inflammatory disease. A subject can also be one who has not been previously diagnosed as having an inflammatory disease; e.g., a subject can be one who exhibits one or more symptoms or risk factors for an inflammatory condition, or a subject who does not exhibit symptoms or risk factors for an inflammatory condition, or a subject who is asymptomatic for inflammatory disease.

A "therapeutic regimen," "therapy" or "therapeutic regimen" or "treatment(s)," as described herein, includes all clinical management of a subject and interventions, whether biological, chemical, physical, or a combination thereof, intended to sustain, ameliorate, improve, or otherwise alter the condition of a subject. These terms may be used synonymously herein. Treatments include but are not limited to administration of prophylactics or therapeutic compounds (including conventional and novel DMARDs, biologic DMARDs, non-steroidal anti-inflammatory drugs (NSAIDs) such as COX-2 selective inhibitors, and corticosteroids), exercise regimens, physical therapy, dietary modification and/or supplementation, bariatric surgical intervention, administration of pharmaceuticals and/or anti-inflammatories (prescription or over-the-counter), and any other treatments known in the art as efficacious in preventing, delaying the onset of, or ameliorating disease. A "response to treatment" includes a subject's response to any of the above-described treatments, whether biological, chemical, physical, or a combination of the foregoing. A "treatment course" relates to the dosage, duration, extent, etc. of a particular treatment or therapeutic regimen. A therapy can be conventional or biologic. Examples of therapies that are generally considered conventional include, but are not limited to, MTX, azathioprine (AZA), bucillamine (BUC), chloroquine (CQ), ciclosporin (CSA, or cyclosporine, or cyclosporin), doxycycline (DOXY), hydroxychloroquine (HCQ), intra-muscular gold (IM gold), leflunomide (LEF), levofloxacin (LEV), and sulfasalazine (SSZ). Examples of other conventional therapies include, but are not limited to, folinic acid, D-pencillamine, gold auranofin, gold aurothioglucose, gold thiomalate, cyclophosphamide, and chlorambucil. Examples of biologic therapies (or biologic drugs) include but are not limited to biological agents that target the tumor necrosis factor (TNF)-alpha molecules and the TNF inhibitors, such as infliximab, adalimumab, etanercept and golimumab. Other classes of biologic therapies include IL1 inhibitors such as anakinra, T-cell modulators such as abatacept, B-cell modulators such as rituximab, and IL6 inhibitors such as tocilizumab.

Figure 8:
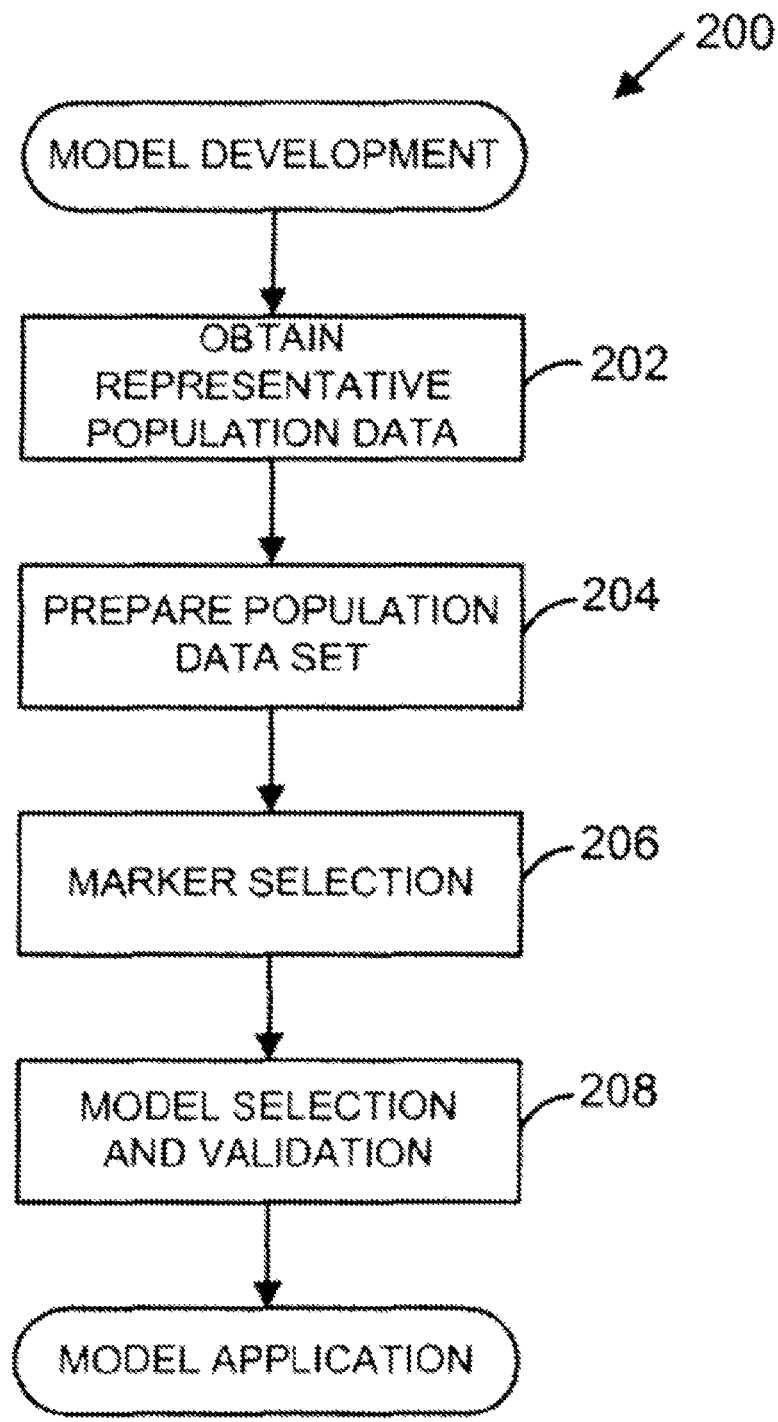
FIG. 8 is a flow diagram, which describes an example of a method for developing a model that can be used to determine the inflammatory disease activity of a person or population.

Use of the Present Teachings in the Diagnosis and Prognosis of Disease, and for Assessing Disease Activity Model Development Process An exemplary method for developing predictive models to determine the inflammatory disease activity of a subject or population is shown by the flow diagram of FIG. 8 (200). Biomarker data from a representative population, as described herein, is obtained (202). This biomarker data can be derived through a variety of methods, including prospective, retrospective, cross-sectional, or longitudinal studies that involve interventions or observations of the representative subjects or populations from one or more time points. The biomarker data can be obtained from a single study or multiple studies. Subject and population data can generally include data pertaining to the subjects' disease status and/or clinical assessments, which can be used for training and validating the algorithms for use in the present teachings, wherein the values of the biomarkers described herein are correlated to the desired clinical measurements.

Data within the representative population dataset is then prepared (204) so as to fit the requirements of the model that will be used for biomarker selection, described below. A variety of methods of data preparation can be used, such as transformations, normalizations, and gap-fill techniques including nearest neighbor interpolation or other pattern recognition techniques. The data preparation techniques that are useful for different model types are well-known in the art.

Biomarkers are then selected for use in the training of the model to determine inflammatory disease activity (206). Various models can be used to inform this selection, and biomarker data are chosen from the dataset providing the most reproducible results. Methods to evaluate biomarker performance can include, e.g., bootstrapping and cross-validation.

After the biomarkers are selected, the model to be used to determine inflammatory disease activity can be selected. For specific examples of statistical methods useful in designing predictive models, see Calculation of the DAI score.

For the particular selection model used with a dataset, biomarkers can be selected based on such criteria as the biomarker's ranking among all candidate markers, the biomarker's statistical significance in the model, and any improvement in model performance when the biomarker is added to the model. Tests for statistical significance can include, for example, correlation tests, t-tests, and analysis of variance (ANOVA). Models can include, for example, regression models such as regression trees and linear models, and classification models such as logistic regression, Random Forest, SVM, tree models, and LDA. Examples of these are described herein.

In those cases where individual biomarkers are not alone indicative of inflammatory disease activity, biomarker combinations can be applied to the selection model. Instead of univariate biomarker selection, for example, multivariate biomarker selection can be used. One example of an algorithm useful in multivariate biomarker selection is a recursive feature selection algorithm. Biomarkers that are not alone good indicators of inflammatory disease activity may still be useful as indicators when in combination with other biomarkers, in a multivariate input to the model, because each biomarker may bring additional information to the combination that would not be informative where taken alone.

Next, selection, training and validation are performed on the model for assessing disease activity (208). Models can be selected based on various performance and/or accuracy criteria, such as are described herein. By applying datasets to different models, the results can be used to select the best models, while at the same time the models can be used to determine which biomarkers are statistically significant for inflammatory disease activity. Combinations of models and biomarkers can be compared and validated in different datasets. The comparisons and validations can be repeated in order to train and/or choose a particular model. Datasets can be used to generate quantitative data, wherein the quantitative data comprises the biomarkers as described herein. The dataset can be compared to a trained dataset representing the biomarkers, and quantitative data can be generated that is derived from the difference between the first and trained dataset.

Figure 9:
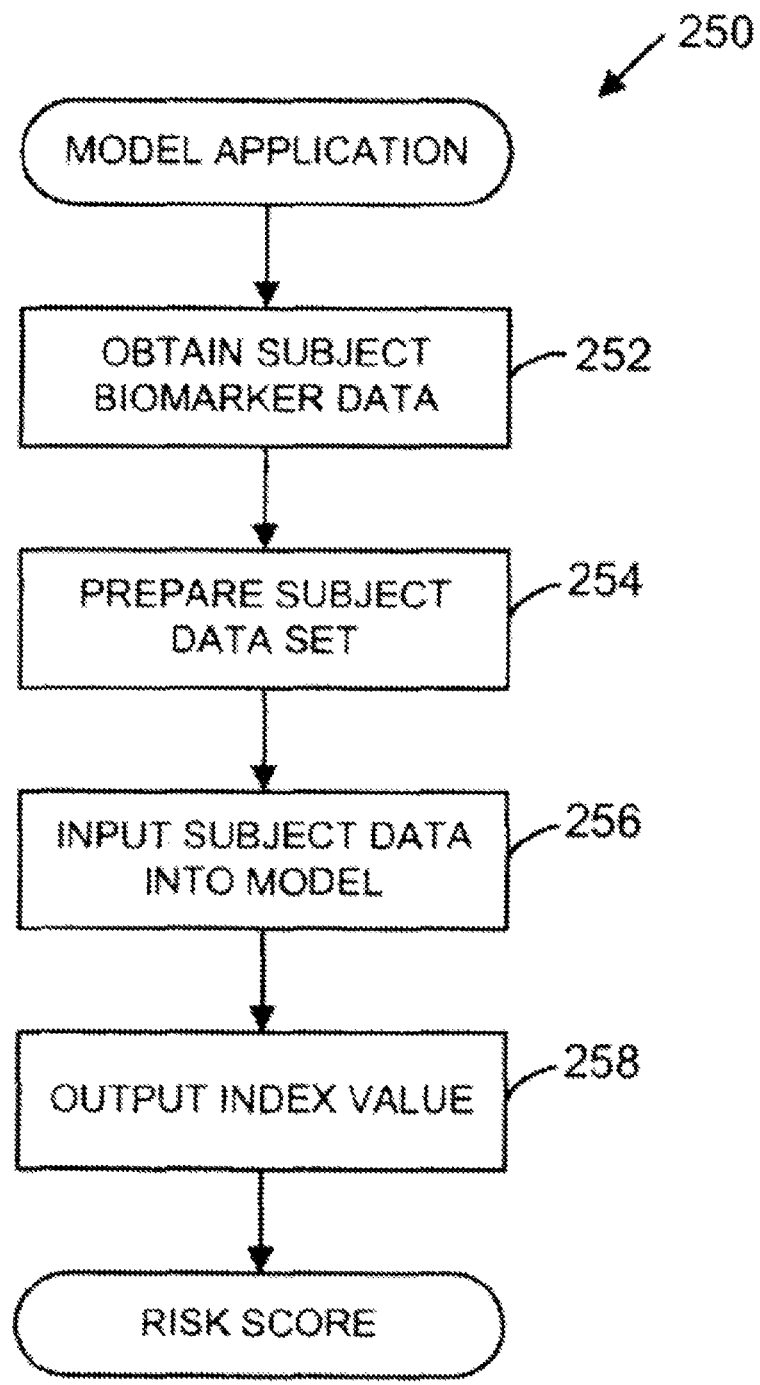
FIG. 9 is a flow diagram, which describes an example of a method for using the model of FIG. 8 to determine the inflammatory disease activity of a subject or population.

FIG. 9 is a flow diagram of an exemplary method (250) of using a model as developed above to determine the inflammatory disease activity of a subject or a population. Biomarker data is obtained from the subject at (252). This data can be obtained by a variety of means, including but not limited to physical examinations, self-reports by the subject, laboratory testing, medical records and charts. Subject data can then be prepared (254) via transformations, logs, normalizations, and so forth, based on the particular model selected and trained in FIG. 8. The data is then input into the model for evaluation (256), which outputs an index value (258); e.g., a DAI score. Examples as to how a model can be used to evaluate a subject's biomarkers and output a DAI value are provided herein.

In some embodiments of the present teachings, the disclosed biomarkers group can be used in the derivation of a DAI score, as described herein, which DAI score can be used to provide diagnosis, prognosis and monitoring of disease state and/or disease activity in inflammatory disease and in autoimmune disease such as JIA. In certain embodiments, the DAI score can be used to provide diagnosis, prognosis and monitoring of disease state and/or disease activity of JIA. In other embodiments, the DAI score can be used to determine molecular remission as a basis for therapy withdraw or tapering.

Identifying the state of inflammatory disease in a subject allows for a prognosis of the disease, and thus for the informed selection of, initiation of, adjustment of or increasing or decreasing various therapeutic regimens in order to delay, reduce or prevent that subject's progression to a more advanced disease state. In some embodiments, therefore, subjects can be identified as having a particular level of inflammatory disease activity and/or as being at a particular state of disease, based at least in part on the determination of their DAI scores, and so can be selected to begin or accelerate treatment, as treatment is defined herein, to prevent or delay the further progression of inflammatory disease. In other embodiments, subjects that are identified via their DAI scores as having a particular level of inflammatory disease activity, and/or as being at a particular state of inflammatory disease, can be selected to have their treatment decreased or discontinued, where improvement or remission in the subject is seen.

Blood-based biomarkers that can be used according to the present teachings to detect the current rate of joint destructive processes can also be applied in a powerful prognostic approach to identifying subjects at highest risk of accelerated bone and cartilage damage. In some embodiments of the present teachings, the disclosed biomarkers can be measured from subjects' or a subject's samples obtained at various time points (e.g., longitudinally), to obtain a series of DAI scores, and the scores can then be combined with radiological results at various time points and so be used to provide a measurement of disease progression. The association of the DAI scores can be analyzed statistically for correlation (e.g., Spearman correlation) using multivariate analysis to create single time point or longitudinal hierarchical linear models and ensure accuracy. Serum biomarkers can thus be used as an alternative to ultrasound, MRI, CT, and radiological results in estimating the risk and rates of progression of disease, and predicting joint damage in JIA. Predictive models using biomarkers can thus be used in diagnostic methods according to the present teachings to identify subjects who need more aggressive treatment, and earlier, and can thereby improve subject outcomes. In other embodiments, the DAI scores from one subject can be compared with each other, for observations of longitudinal trending as an effect of, e.g., choice or effectiveness of therapeutic regimen, or as a result of the subject's response to treatment regimens, or a comparison of the subject's responses to different regimens.

The present teachings indicate that the disclosed biomarkers are a strong predictor of disease activity over time; e.g., longitudinally. This is a significant finding from a clinical care perspective. Currently no tests are available to accurately measure and track JIA disease activity over time in the clinic. The tests developed from various embodiments of the present teachings will facilitate the monitoring of disease activity and Tight Control practices, and result in improved control of disease activity and improved clinical outcomes.

Regarding the need for early and accurate diagnosis of JIA, recent advances in JIA treatment provide a means for more profound disease management and optimal treatment of JIA within the first months of symptom onset, which in turn result in significantly improved outcomes. Unfortunately, most subjects do not receive optimal treatment within this narrow window of opportunity, resulting in poorer outcomes and irreversible joint damage, in part because of the limits of current diagnostic laboratory tests. Numerous difficulties exist in diagnosing JIA in a subject. This is in part because at their early stages, symptoms may not be fully differentiated. It is also because diagnostic tests for JIA were developed based on phenomenological findings, not the biological basis of disease. In various embodiments of the present teachings, multi-biomarker algorithms useful in diagnostic methods for detecting JIA can be derived from the disclosed biomarkers. This aspect of the present teachings has the potential to improve both the accuracy of JIA diagnosis, and the speed of JIA detection.

Classifying Disease Activity

In some embodiments of the present teachings, the DAI score, derived as described herein, can be used to classify or score inflammatory disease activity; e.g., as high, medium, low, or remission. In some embodiments of the present teachings, autoimmune disease activity can be so classified or scored. In other embodiments, JIA disease activity can be so classified or scored. Using JIA disease as an example, because the DAI score correlates well and with high accuracy with clinical assessments of JIA (e.g., with a JADAS score), DAI cut-off scores can be set at predetermined levels to indicate levels of JIA disease activity, and to correlate with the cut-offs traditionally established for rating JIA activity via JADAS scores. Because the DAI score correlates well with traditional clinical assessments of inflammatory disease activity, e.g. in JIA, in other embodiments of the present teachings bone damage itself in a subject or population, and thus disease progression, can be tracked via the use and application of the DAI score. In other words, the present teachings disclose methods of detecting or measuring damage (and/or disease progression) by determining a patient sample's DAI score as a surrogate for (e.g., in place of) traditional clinical assessments.

These properties of the disclosed biomarkers can be used for several purposes. On a subject-specific basis, they provide a context for understanding the relative level of disease activity. The rating of disease activity can be used, e.g., to guide the clinician in determining treatment, in setting a treatment course, and/or to inform the clinician that the subject is in remission. Moreover, it provides a means to more accurately assess and document the qualitative level of disease activity in a subject. It is also useful from the perspective of assessing clinical differences among populations of subjects within a practice. For example, this tool can be used to assess the relative efficacy of different treatment modalities. Moreover, it is also useful from the perspective of assessing clinical differences among different practices. This would allow physicians to determine what global level of disease control is achieved by their colleagues, and/or for healthcare management groups to compare their results among different practices for both cost and comparative effectiveness.

Subject Screening

Certain embodiments of the present teachings can also be used to screen subject populations in any number of settings. For example, a health maintenance organization, public health entity or school health program can screen a group of subjects to identify those requiring interventions, as described above. Other embodiments of these teachings can be used to collect disease activity data on one or more populations of subjects, to identify subject disease status in the aggregate, in order to, e.g., determine the effectiveness of the clinical management of a population, or determine gaps in clinical management. Insurance companies (e.g., health, life, or disability) may request the screening of applicants in the process of determining coverage for possible intervention. Data collected in such population screens, particularly when tied to any clinical progression to conditions such as inflammatory disease and JIA, will be of value in the operations of, for example, health maintenance organizations, public health programs and insurance companies.

Such data arrays or collections can be stored in machine-readable media and used in any number of health-related data management systems to provide improved healthcare services, cost-effective healthcare, and improved insurance operation, among other things. See, e.g., U.S. Patent Application No. 2002/0038227; U.S. Patent Application No. 2004/0122296; U.S. Patent Application No. 2004/0122297; and U.S. Pat. No. 5,018,067. Such systems can access the data directly from internal data storage or remotely from one or more data storage sites as further detailed herein. Thus, in a health-related data management system, wherein it is important to manage inflammatory disease progression for a population in order to reduce disease-related employment productivity loss, disability and surgery, and thus reduce healthcare costs in the aggregate, various embodiments of the present teachings provide an improvement comprising the use of a data array encompassing the biomarker measurements as defined herein, and/or the resulting evaluation of disease status and activity from those biomarker measurements.

Measuring Accuracy and Performance of the Present Teachings

The performance of the present teachings can be assessed in any of various ways. Assessing the performance of an embodiment of the present teachings can provide a measurement of the accuracy of that embodiment, where, e.g., that embodiment is a predictive model, or a test, assay, method or procedure, whether diagnostic or prognostic. This accuracy assessment can relate to the ability of the predictive model or the test to determine the inflammatory disease activity status of a subject or population. In other embodiments, the performance assessment relates to the accuracy of the predictive model or test in distinguishing between subjects with or without inflammatory disease. In other embodiments, the assessment relates to the accuracy of the predictive model or test in distinguishing between states of inflammatory disease in one subject at different time points.

The distinguishing ability of the predictive model or test can be based on whether the subject or subjects have a significant alteration in the levels of one or more biomarkers. In some embodiments a significant alteration, in the context of the present teachings, can mean that the measurement of the biomarkers, as represented by the DAI score computed by the DAI formula as generated by the predictive model, is different than some predetermined DAI cut-off point (or threshold value) for those biomarkers when input to the DAI formula as described herein. This significant alteration in biomarker levels as reflected in differing DAI scores can therefore indicate that the subject has inflammatory disease, or is at a particular state or severity of inflammatory disease. The difference in the levels of biomarkers between the subject and normal, in those embodiments where such comparisons are done, is preferably statistically significant, and can be an increase in biomarker level or levels, or a decrease in biomarker level or levels. In some embodiments of the present teachings, a significant alteration can mean that a DAI score is derived from measuring the levels of one or more biomarkers, and this score alone, without comparison to some predetermined cut-off point (or threshold value) for those biomarkers, indicates that the subject has inflammatory disease or has a particular state of inflammatory disease. Further, achieving increased analytical and clinical accuracy may require that combinations of three or more biomarkers be used together in panels, and combined with mathematical algorithms derived from predictive models to obtain the DAI score.

Use of statistical values such as the area under the curve (AUC), and specifically the AUC as it relates to the receiver/operator curve (ROC), encompassing all potential threshold or cut-off point values is generally used to quantify predictive model performance. Acceptable degrees of accuracy can be defined. In certain embodiments of the present teachings, an acceptable degree of accuracy can be one in which the AUC for the ROC is 0.60 or higher.

In general, defining the degree of accuracy for the relevant predictive model or test (e.g., cut-off points on a ROC), defining an acceptable AUC value, and determining the acceptable ranges in relative concentration of what constitutes an effective amount of the biomarkers of the present teachings, allows one of skill in the art to use the biomarkers of the present teachings to identify inflammatory disease activity in subjects or populations with a pre-determined level of predictability and performance.

In various embodiments of the present teachings, measurements from multiple biomarkers can be combined into a single value, the DAI score, using various statistical analyses and modeling techniques as described herein. Because the DAI score demonstrates strong association with established disease activity assessments, such as JADAS, the DAI score can provide a quantitative measure for monitoring the extent of subject disease activity, and response to treatment.

Calculation of the DAI Score

In some embodiments of the present teachings, inflammatory disease activity in a subject is measured by: determining the levels in inflammatory disease subject serum of three or more biomarkers, then applying an interpretation function to transform the biomarker levels into a single DAI score, which provides a quantitative measure of inflammatory disease activity in the subject. As discussed above and demonstrated in the Examples below, a DAI score derived in this way according to the present teachings correlates well with traditional clinical and diagnostic assessments of inflammatory disease activity (e.g., a JADAS score in JIA) and thus can be used as a diagnostic score to measure disease activity. In some embodiments, the disease activity so measured relates to an autoimmune disease. In some embodiments, the disease activity so measured relates to JIA.

In some embodiments, the interpretation function is based on a predictive model. Established statistical algorithms and methods well-known in the art, useful as models or useful in designing predictive models, can include but are not limited to: analysis of variants (ANOVA); Bayesian networks; boosting and Ada-boosting; bootstrap aggregating (or bagging) algorithms; decision trees classification techniques, such as Classification and Regression Trees (CART), boosted CART, Random Forest (RF), Recursive Partitioning Trees (RPART), and others; Curds and Whey (CW); Curds and Whey-Lasso; dimension reduction methods, such as principal component analysis (PCA) and factor rotation or factor analysis; discriminant analysis, including Linear Discriminant Analysis (LDA), Eigengene Linear Discriminant Analysis (ELDA), and quadratic discriminant analysis; Discriminant Function Analysis (DFA); factor rotation or factor analysis; genetic algorithms; Hidden Markov Models; kernel based machine algorithms such as kernel density estimation, kernel partial least squares algorithms, kernel matching pursuit algorithms, kernel Fisher's discriminate analysis algorithms, and kernel principal components analysis algorithms; linear regression and generalized linear models, including or utilizing Forward Linear Stepwise Regression, Lasso (or LASSO) shrinkage and selection method, and Elastic Net regularization and selection method; glmnet (Lasso and Elastic Net-regularized generalized linear model); Logistic Regression (LogReg); meta-learner algorithms; nearest neighbor methods for classification or regression, e.g. Kth-nearest neighbor (KNN); non-linear regression or classification algorithms; neural networks; partial least square; rules based classifiers; shrunken centroids (SC); sliced inverse regression; Standard for the Exchange of Product model data, Application Interpreted Constructs (StepAIC); super principal component (SPC) regression; and, Support Vector Machines (SVM) and Recursive Support Vector Machines (RSVM), among others. Additionally, clustering algorithms as are known in the art can be useful in determining subject sub-groups.

Logistic Regression is the traditional predictive modeling method of choice for dichotomous response variables; e.g., treatment 1 versus treatment 2. It can be used to model both linear and non-linear aspects of the data variables and provides readily interpretable odds ratios.

Discriminant Function Analysis (DFA) uses a set of analytes as variables (roots) to discriminate between two or more naturally occurring groups. DFA is used to test analytes that are significantly different between groups. A forward step-wise DFA can be used to select a set of analytes that maximally discriminate among the groups studied. Specifically, at each step all variables can be reviewed to determine which will maximally discriminate among groups. This information is then included in a discriminative function, denoted a root, which is an equation consisting of linear combinations of analyte concentrations for the prediction of group membership. The discriminatory potential of the final equation can be observed as a line plot of the root values obtained for each group. This approach identifies groups of analytes whose changes in concentration levels can be used to delineate profiles, diagnose and assess therapeutic efficacy. The DFA model can also create an arbitrary score by which new subjects can be classified as either "healthy" or "diseased." To facilitate the use of this score for the medical community the score can be rescaled so a value of 0 indicates a healthy individual and scores greater than 0 indicate increasing disease activity.

Classification and regression trees (CART) perform logical splits (if/then) of data to create a decision tree. All observations that fall in a given node are classified according to the most common outcome in that node. CART results are readily interpretable—one follows a series of if/then tree branches until a classification results.

Support vector machines (SVM) classify objects into two or more classes. Examples of classes include sets of treatment alternatives, sets of diagnostic alternatives, or sets of prognostic alternatives. Each object is assigned to a class based on its similarity to (or distance from) objects in the training data set in which the correct class assignment of each object is known. The measure of similarity of a new object to the known objects is determined using support vectors, which define a region in a potentially high dimensional space (>R6).

The process of bootstrap aggregating, or "bagging," is computationally simple. In the first step, a given dataset is randomly resampled a specified number of times (e.g., thousands), effectively providing that number of new datasets, which are referred to as "bootstrapped resamples" of data, each of which can then be used to build a model. Then, in the example of classification models, the class of every new observation is predicted by the number of classification models created in the first step. The final class decision is based upon a "majority vote" of the classification models; i.e., a final classification call is determined by counting the number of times a new observation is classified into a given group, and taking the majority classification (33%+ for a three-class system). In the example of logistical regression models, if a logistical regression is bagged 1000 times, there will be 1000 logistical models, and each will provide the probability of a sample belonging to class 1 or 2.

Curds and Whey (CW) using ordinary least squares (OLS) is another predictive modeling method. See L. Breiman and J H Friedman, *J. Royal. Stat. Soc. B* 1997, 59(1):3-54. This method takes advantage of the correlations between response variables to improve predictive accuracy, compared with the usual procedure of performing an individual regression of each response variable on the common set of predictor variables X. In CW, Y=XB*S, where Y=($y_{kj}$) with k for the $k^{th}$ patient and j for $j^{th}$ response (j=1 for TJC, j=2 for SJC, etc.), B is obtained using OLS, and S is the shrinkage matrix computed from the canonical coordinate system. Another method is Curds and Whey and Lasso in combination (CW-Lasso). Instead of using OLS to obtain B, as in CW, here Lasso is used, and parameters are adjusted accordingly for the Lasso approach.

Many of these techniques are useful either combined with a biomarker selection technique (such as, for example, forward selection, backwards selection, or stepwise selection), or for complete enumeration of all potential panels of a given size, or genetic algorithms, or they can themselves include biomarker selection methodologies in their own techniques. These techniques can be coupled with information criteria, such as Akaike's Information Criterion (AIC), Bayes Information Criterion (BIC), or cross-validation, to quantify the tradeoff between the inclusion of additional biomarkers and model improvement, and to minimize overfit. The resulting predictive models can be validated in other studies, or cross-validated in the study they were originally trained in, using such techniques as, for example, Leave-One-Out (LOO) and 10-Fold cross-validation (10-Fold CV).

In some embodiments of the present teachings, it is not required that the DAI score be compared to any predetermined "reference," "normal," "control," "standard," "healthy," "pre-disease" or other like index, in order for the DAI score to provide a quantitative measure of inflammatory disease activity in the subject.

In other embodiments of the present teachings, the amount of the biomarker(s) can be measured in a sample and used to derive a DAI score, which DAI score is then compared to a "normal" or "control" level or value, utilizing techniques such as, e.g., reference or discrimination limits or risk defining thresholds, in order to define cut-off points and/or abnormal values for inflammatory disease. The normal level then is the level of one or more biomarkers or combined biomarker indices (e.g., DAI score) typically found in a subject who is not suffering from the inflammatory disease under evaluation or in whom disease activity is known to be some particular (e.g., clinically acceptable) level. Other terms for "normal" or "control" are, e.g., "reference," "index," "baseline," "standard," "healthy," "pre-disease," etc. Such normal levels can vary, based on whether a biomarker is used alone or in a formula combined with other biomarkers to output a score. Alternatively, the normal level can be a database of biomarker patterns from previously tested subjects who did not convert to the inflammatory disease under evaluation over a clinically relevant time period. Reference (normal, control) values can also be derived from, e.g., a control subject or population whose inflammatory disease activity level or state is known. In some embodiments of the present teachings, the reference value can be derived from one or more subjects who have been exposed to treatment for inflammatory disease, or from one or more subjects who are at low risk of developing inflammatory disease, or from subjects who have shown improvements in inflammatory disease activity factors (such as, e.g., clinical parameters as defined herein) as a result of exposure to treatment. In some embodiments the reference value can be derived from one or more subjects who have not been exposed to treatment; for example, samples can be collected from (a) subjects who have received initial treatment for inflammatory disease, and (b) subjects who have received subsequent treatment for inflammatory disease, to monitor the progress of the treatment. A reference value can also be derived from disease activity algorithms or computed indices from population studies.

Systems for Implementing Disease Activity Tests

Tests for measuring disease activity according to various embodiments of the present teachings can be implemented on a variety of systems typically used for obtaining test results, such as results from immunological or nucleic acid detection assays. Such systems may comprise modules that automate sample preparation, that automate testing (e.g., measuring biomarker levels), that facilitate testing of multiple samples, and/or are programmed to assay the same test or different tests on each sample. In some embodiments, the testing system comprises one or more of a sample preparation module, a clinical chemistry module, and an immunoassay module on one platform. Testing systems can be designed such that they also comprise modules to collect, store, and track results, such as by connecting to and utilizing a database residing on hardware. Examples of these modules include physical and electronic data storage devices as are known in the art, such as a hard drive, flash memory, and magnetic tape. Test systems also generally comprise a module for reporting and/or visualizing results. Some examples of reporting modules include a visible display or graphical user interface, links to a database, a printer, etc. See section Machine-readable storage medium, below.

One embodiment of the present invention comprises a system for determining the inflammatory disease activity of a subject. In some embodiments, the system employs a module for applying a formula to an input comprising the measured levels of biomarkers in a panel, as described herein, and outputting a disease activity index score. In some embodiments, the measured biomarker levels are test results, which serve as inputs to a computer that is programmed to apply the formula. The system may comprise other inputs in addition to or in combination with biomarker results in order to derive an output disease activity index; e.g., one or more clinical parameters such as therapeutic regimen, TJC, SJC, morning stiffness, arthritis of three or more joint areas, arthritis of hand joints, symmetric arthritis, rheumatoid nodules, radiographic changes and other imaging, gender/sex, age, race/ethnicity, disease duration, height, weight, body-mass index, family history, CCP status, RF status, ESR, smoker/non-smoker, etc. In some embodiments the system can apply the formula to biomarker level inputs, and then output a disease activity score that can then be analyzed in conjunction with other inputs such as other clinical parameters. In other embodiments, the system is designed to apply the formula to the biomarker and non-biomarker inputs (such as clinical parameters) together, and then report a composite output disease activity index.

A number of testing systems are presently available that can be used to implement various embodiments of the present teachings. See, for example, the ARCHITECT series of integrated immunochemistry systems—high-throughput, automated, clinical chemistry analyzers (ARCHITECT is a registered trademark of Abbott Laboratories, Abbott Park, Ill. 60064). See C. Wilson et al., "Clinical Chemistry Analyzer Sub-System Level Performance," American Association for Clinical Chemistry Annual Meeting, Chicago, Ill., Jul. 23-27, 2006; and, H J Kisner, "Product development: the making of the Abbott ARCHITECT," Clin. Lab. Manage.

Rev. 1997 November-December, 11(6):419-21; A. Ognibene et al., "A new modular chemiluminescence immunoassay analyser evaluated," Clin. Chem. Lab. Med. 2000 March, 38(3):251-60; J W Park et al., "Three-year experience in using total laboratory automation system," Southeast Asian J. Trop. Med. Public Health 2002, 33 Suppl 2:68-73; D. Pauli et al., "The Abbott Architect c8000: analytical performance and productivity characteristics of a new analyzer applied to general chemistry testing," Clin. Lab. 2005, 51(1-2):31-41.

Another testing system useful for embodiments of the present teachings is the VITROS system (VITROS is a registered trademark of Johnson & Johnson Corp., New Brunswick, N.J.)—an apparatus for chemistry analysis that is used to generate test results from blood and other body fluids for laboratories and clinics. Another testing system is the DIMENSION system (DIMENSION is a registered trademark of Dade Behring Inc., Deerfield Ill.)—a system for the analysis of body fluids, comprising computer software and hardware for operating the analyzers, and analyzing the data generated by the analyzers.

The testing required for various embodiments of the present teachings, e.g. measuring biomarker levels, can be performed by laboratories such as those certified under the Clinical Laboratory Improvement Amendments (42 U.S.C. Section 263(a)), or by laboratories certified under any other federal or state law, or the law of any other country, state or province that governs the operation of laboratories that analyze samples for clinical purposes.

Biomarker Selection

The biomarkers and methods of the present teachings allow one of skill in the art to monitor or assess a subject's inflammatory and/or autoimmune disease activity, such as for JIA, with a high degree of accuracy. For the initial comparison of observed biomarker with JIA disease activity, the disease activity for each subject was based upon clinical parameters, such as the JADAS score.

DAIMRK Group of Markers

Analyte biomarkers can be selected for use in the present teachings to form a panel or group of markers. Table 1 describes several specific biomarkers, collectively referred to as the DAIMRK group of biomarkers. The present teachings describe the set of biomarkers as one set or panel of markers that is strongly associated with inflammatory disease, and especially JIA, when used in particular combinations to derive a DAI score, based on their correlation with traditional clinical assessments of disease; in the example of JIA, by their correlation with JADAS. See Example 1. Methods of determining JIA disease activity can comprise measuring the levels of, for example, at least 1, 2, 3, 4, 5, 6, 7, 8, 9, 10, 11, 12, 13, 14, 15, 16, 17, 18, 19, 20, 25, 30, 35, 40, 45, or 50 biomarkers from Table 1. As an example, one embodiment of the present teachings comprises a method of determining JIA disease activity in a subject comprising measuring the levels of at least three biomarkers from Table 1, wherein the at least three biomarkers are selected from the group consisting of alpha-2-macroglobulin (A2M); amyloid P component, serum (SAP); angiopoietin 1 (AGP1) antithrombin III (ATIII); ataxia telangiectasia mutated (ATM); B-cell activating factor (BAFF); chemokine (C-C motif) ligand 2 (CCL2); chemokine (C-C motif) ligand 3 (CCL3); chemokine (C-C motif) ligand 11 (CCL11); chemokine (C-C motif) ligand 22 (CCL22); chemokine (C-X-C motif) ligand 9 (CXCL9); chemokine (C-X-C motif) ligand 10 (CXCL10); CD40 ligand (CD40LG); C-reactive protein (CRP); complement C3; complement C4; complement factor H (CFH); epidermal growth factor (EGF); gelsolin (GSN); granzyme (GZM); haptoglobin (HP); heat shock protein 60 (HSP60); interleukin 6 (IL6); leptin (LEP); MF; matrix metalloproteinase-1 (MMP1); matrix metalloproteinase-3 (MMP3); matrix metalloproteinase-9 (MMP9); resistin (RETN); serum amyloid (SAA); tumor necrosis factor receptor, type 1 (TNF-R1); vascular cell adhesion molecule-1 (VCAM1); vascular endothelial growth factor A (VEGF-A); Calprotectin; intercellular adhesion molecule 1 (ICAM-1); interleukin-1 beta (IL-1B); interleukin-6 receptor (IL-6R); interleukin-8 (IL-8); interleukin-8 (IL-10); interleukin-8 (IL-17); interleukin-8 (IL-18); interleukin-8 (IL-21); L-selectin; MDC; P-selectin; pyridinoline (PYD); S100 A12; S100A14; TIMP metallopeptidase inhibitor 1 (TIMP1); TNF receptor-associated protein 1 (TRAP-1); transthyretin (TTR); tumor protein 53 (TP53); and YKL-40; then, using these observed biomarker levels to derive a disease activity index score for the subject via an interpretation function, which score provides a quantitative measure of JIA disease activity in that subject.

One skilled in the art will recognize that the biomarkers presented herein encompass all forms and variants of these biomarkers, including but not limited to polymorphisms, isoforms, mutants, derivatives, transcript variants, precursors (including nucleic acids and pre- or pro-proteins), cleavage products, receptors (including soluble and transmembrane receptors), ligands, protein-ligand complexes, protein-protein homo- or heteropolymers, post-translationally modified variants (such as, e.g., via cross-linking or glycosylation), fragments, and degradation products, as well as any multi-unit nucleic acid, protein, and glycoprotein structures comprising any of the biomarkers as constituent subunits of the fully assembled structure.

TABLE 1

| Adhesion Molecules | Growth Factors | Cytokines/ Chemokines | Hormones | Matrix Metalloproteinases | Skeletal-related Proteins | Acute Phase Proteins | Other |
|---|---|---|---|---|---|---|---|
| VCAM-1 | EGF | IL-1B | Leptin | MMP-1 | YKL-40 | SAA | Calprotectin |
| ICAM-1 | VEGF-A | IL-6 | Resistin | MMP-3 | PYD | CRP | S100 A12 |
| P-selectin | TRAP1 | IL-8 | | MMP-9 | | SAP | S100 A14 |
| L-selectin | | IL-10 | | TIMP-1 | | | HSP60 |
| | | IL-18 | | | | | A2M |
| | | IL-17 | | | | | ATIII |
| | | IL-21 | | | | | HP |
| | | BAFF | | | | | AGP1 |
| | | CCL2 | | | | | MF |
| | | CCL3 | | | | | TP53 |
| | | CCL11 | | | | | ATM |
| | | CXCL9 | | | | | GZM |
| | | CXCL10 | | | | | TTR |

TABLE 1-continued

| Adhesion Molecules | Growth Factors | Cytokines/ Chemokines | Hormones | Matrix Metallo- proteinases | Skeletal- related Proteins | Acute Phase Proteins | Other |
|---|---|---|---|---|---|---|---|
| | | CCL22 TNF-R1 IL-6R CD40LG | | | | | CFH Complement C3 Complement C4 GSN |

Table 2: Candidate Biomarkers—Biomarker Name (NCBI RefSeq)

As described in Example 1, a strong correlation between the 12 biomarker VECTRA™ DA MBDA panel score and JADAS was observed at r=0.77 (FIG. 1). There was also a high degree of correlation between the 12 biomarker VECTRA™ DA MBDA panel score with JADAS components. For example, the correlation between the 12 biomarker VECTRA™ DA MBDA panel score and the Physician's Global Assessment was r=0.71; the correlation between the 12 biomarker VECTRA™ DA MBDA panel and the Parent's Global Assessment was r=0.61; and the correlation between the 12 biomarker VECTRA™ DA MBDA panel and Active Joint Counts was r=0.62 (FIG. 1).

Figure 5A:
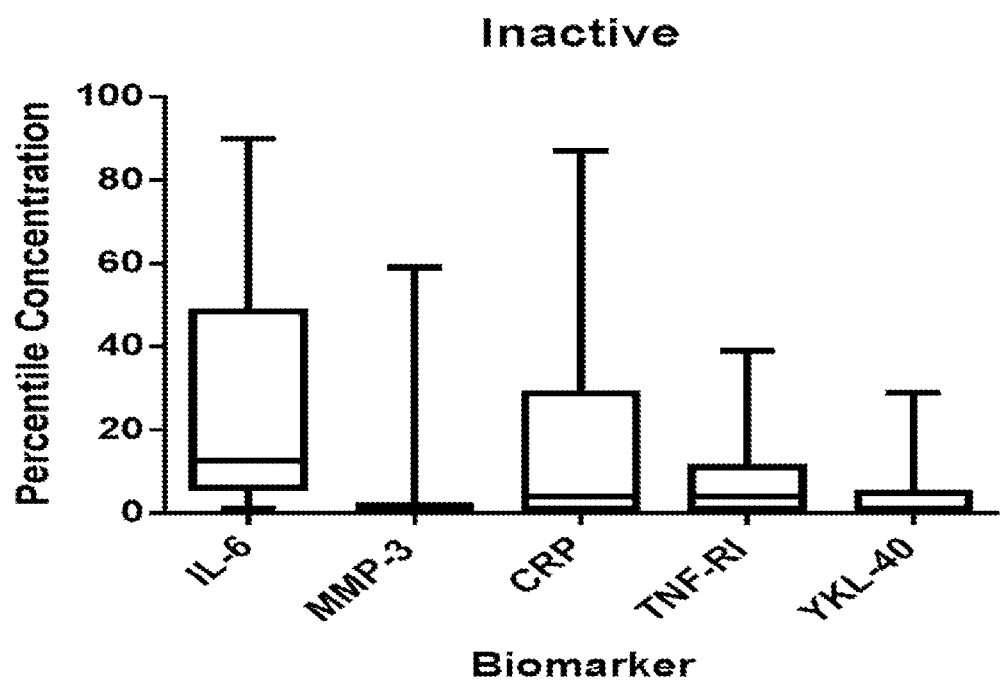
FIG. 5A illustrates differences in selected biomarkers for Inactive. Boxes represent interquartile ranges; whiskers represent min-max.
Figure 5B:
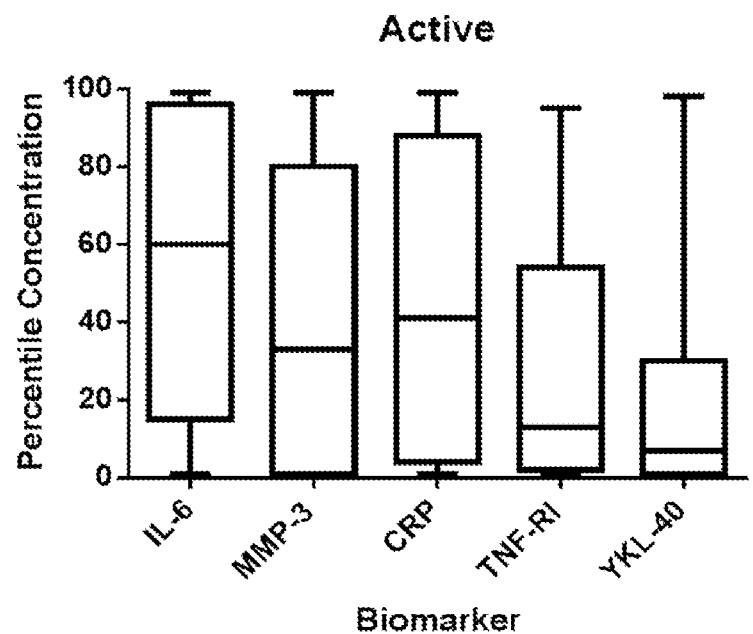
FIG. 5B illustrates differences in selected biomarkers for Active Disease. Boxes represent interquartile ranges; whiskers represent min-max.
Figure 5C:
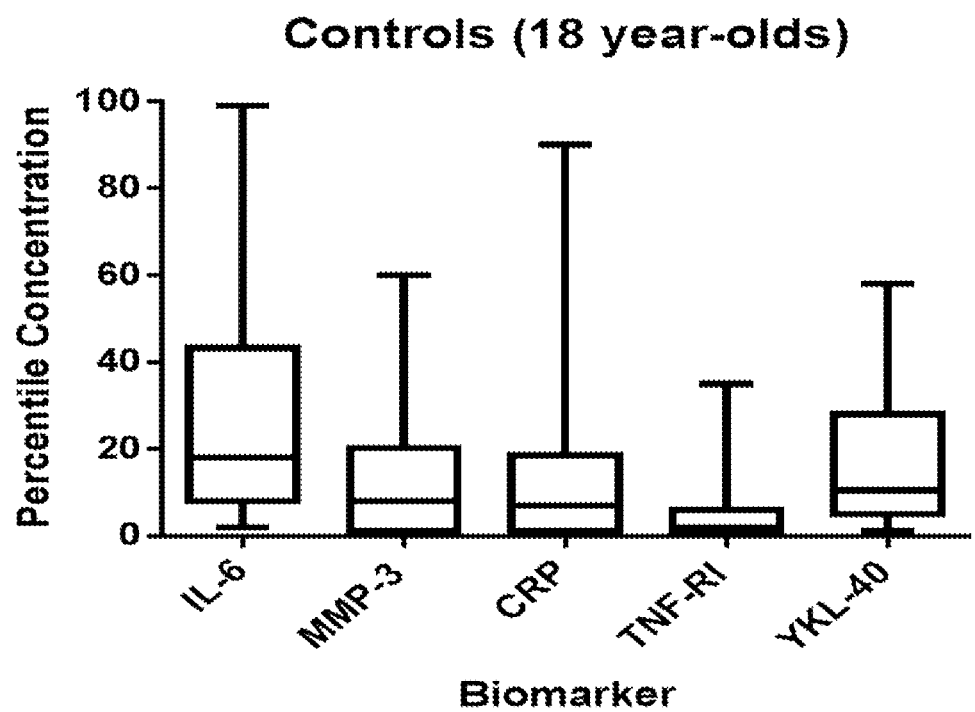
FIG. 5C illustrates differences in selected biomarkers for non-disease controls. Boxes represent interquartile ranges; whiskers represent min-max.
Figure 6A:
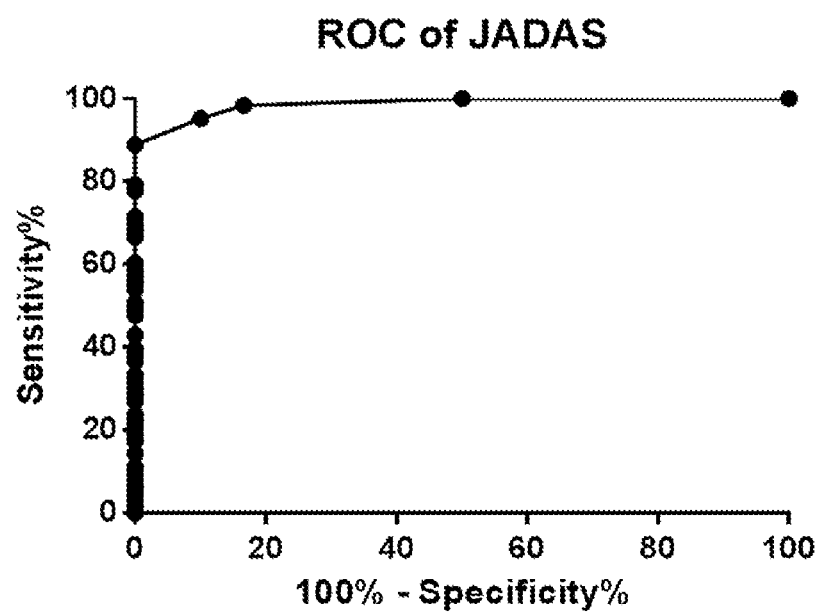
FIG. 6A illustrates the AUROC for Active vs. Inactive Disease ROC for JADAS.
Figure 6B:
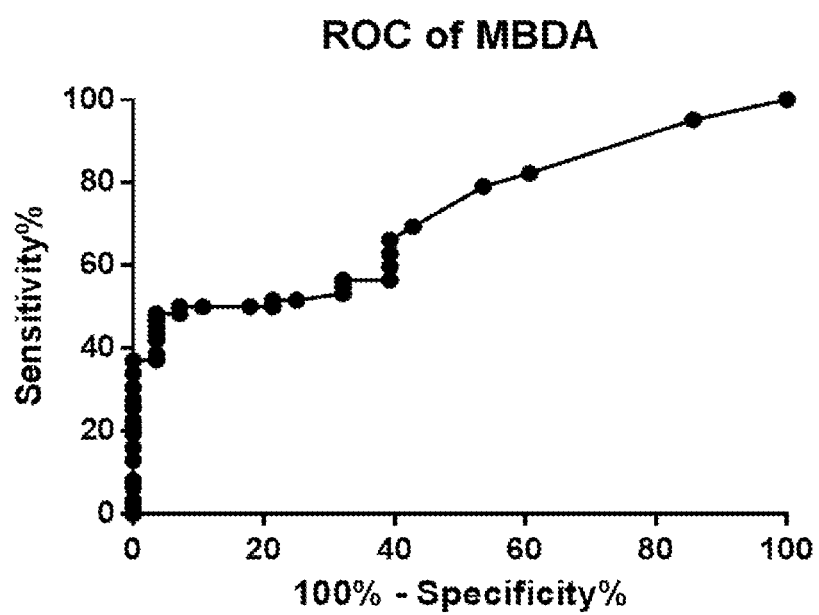
FIG. 6B illustrates the AUROC for Active vs. the VECTRA™ DA MBDA biomarker panel.
Figure 7A:
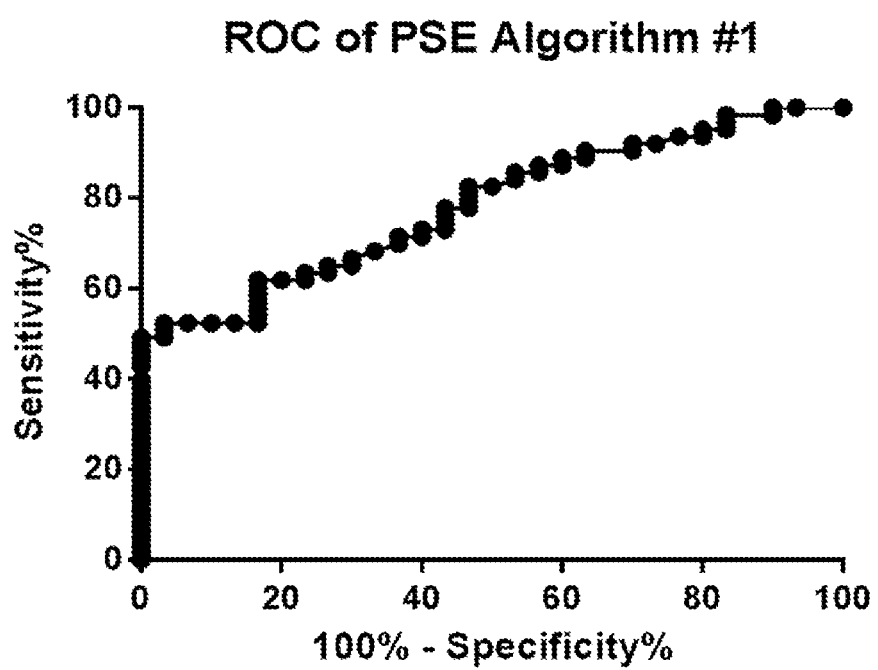
FIG. 7A illustrates the AUROC for Active vs. Inactive Disease ROC for a 9 or 10 biomarker panel comprising IL-6, MMP3, CRP, TNF-R1, with or w/o Calprotectin, YKL-40, ICAM-1, SAA, VCAM-1 and MMP1 with Calprotectin.
Figure 7B:
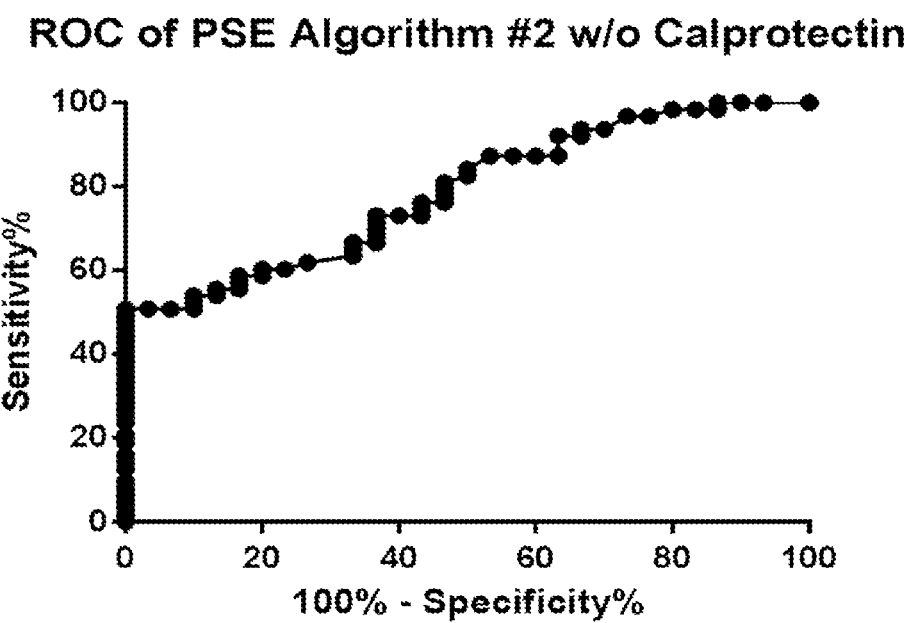
FIG. 7B illustrates the AUROC for Active vs. Inactive Disease ROC for a 9 or 10 biomarker panel comprising IL-6, MMP3, CRP, TNF-R1, with or w/o Calprotectin, YKL-40, ICAM-1, SAA, VCAM-1 and MMP1 without Calprotectin.

There was a further strong correlation between a 9 or 10 biomarker panel comprising IL-6, MMP3, CRP, TNF-R1, with or w/o Calprotectin, YKL-40, ICAM-1, SAA, VCAM-1 and MMP1. Use of different algorithms further demonstrated strong correlations between MBDA and JADAS. FIG. 2 demonstrates that this panel shows that the correlation between the 9 or 10 biomarker panel with or without Calprotectin and JADAS was r=0.85 (top panels). Furthermore FIG. 2 demonstrates that the 10 biomarker panel with Calprotectin and the Physician's Global Assessment was r=0.80 (lower left panel), and the 9 biomarker panel without Calprotectin and the Physician's Global Assessment was r=0.81 (lower right panel). Additionally, several individual biomarkers, including IL-6, MMP-3, TNF-R1, Calprotectin and YKL-40, exhibited higher concentrations in the active disease group compared with the CID group (FIG. 3). The performance of the biomarkers were further evaluated as a function of ACR disease status and compared to a set of 59 unaffected individual 18 years of age. The mean and median MBDA scores for the normal controls were 14 and 17, respectively. For the ACR inactive disease group (n=18) mean and median MBDA scores were 14 and 21, and the active disease group (n=6) were 36 and 39. The level of the biomarkers is presented in FIG. 5 as the percentile of the InFoRM RA population. The biomarker profiles for the normal population and ACR inactive disease populations appear very similar. In contrast, individual biomarkers, such as SAA, CRP, IL-6, and MMP-3, were elevated in the active disease group and unaffected normal relative to active disease.

Biological Significance of the Disclosed Biomarkers

The present teachings describe a robust, stepwise development process for identifying a panel or panels of biomarkers that are strongly predictive of autoimmune disease activity. Multivariate algorithmic combinations of specific biomarkers as described herein exceed the prognostic and predictive power of individual biomarkers known in the art, because the combinations comprise biomarkers that represent a broad range of disease mechanisms, which no individual biomarker does. As a consequence of the diversity of pathways represented by the combinations as taught herein, the methods of the present teachings are useful in the clinical assessment of individual subjects, despite the heterogeneity of the pathology of the disease assessed.

The group of biomarkers described herein was identified through a selection process comprising rigorous correlation studies of an initial large, comprehensive set of candidate protein biomarkers. The methodology employed in selecting the biomarkers resulted in a set of markers especially useful in quantifying JIA disease activity, by providing the clinician with a unique and broad look at JIA disease biology. The biomarkers of the present teachings are thus more effective in quantifying disease activity than single biomarkers or randomly selected groupings of biomarkers.

Additionally, because the serum levels of certain protein biomarkers are known to fluctuate in an individual, depending on disease activity, in some embodiments of the present teachings the clinician could select those biomarkers for generating a DAI score, and thus obtain a more concise overview of the subject's present disease activity status.

Moreover, the process of comprehensive candidate biomarker identification and subsequent staged correlation-based analyses in a series of independent cohorts, as described in the Examples that follow, results in the identification of a panel or panels of biomarkers that have significant correlation to disease activity.

Modifications for Response to Treatment

In certain embodiments of the present teachings, the disclosed biomarkers can be used to determine a subject's response to treatment for inflammatory disease such as JIA.

Reference Standards for Treatment

In many embodiments, the levels of one or more analyte biomarkers or the levels of a specific panel of analyte biomarkers in a sample are compared to a reference standard ("reference standard" or "reference level") in order to direct treatment decisions. The reference standard used for any embodiment disclosed herein may comprise average, mean, or median levels of the one or more analyte biomarkers or the levels of the specific panel of analyte biomarkers in a control population. The reference standard may additionally comprise cutoff values or any other statistical attribute of the control population, such as a standard deviation from the mean levels of the one or more analyte biomarkers or the levels of the specific panel of analyte biomarkers. In some embodiments, the control population may comprise healthy individuals or individuals with JIA.

In some embodiments, individuals with levels of one or more analyte biomarkers or levels of a specific panel of analyte biomarkers greater than the reference levels would be more likely to have higher JIA disease activity. Therefore, an individual presenting with levels of the one or more analyte biomarkers or levels of the specific panel of analyte biomarkers greater than the reference standard would be a candidate for more aggressive therapy. On the other hand, an individual presenting with levels of the one or more analyte biomarkers or levels of the specific panel of analyte biomarkers less than or equal to the reference standard would be less likely to have JIA disease activity and therefore be a candidate for less aggressive therapy.

In other embodiments, individuals with levels of one or more analyte biomarkers or levels of a specific panel of analyte biomarkers less than the reference levels would be more likely to have high JIA disease activity. Therefore, an individual presenting with levels of the one or more analyte biomarkers or levels of the specific panel of analyte biomarkers less than the reference standard would be a candidate for more aggressive therapy. On the other hand, an individual presenting with levels of the one or more analyte biomarkers or levels of the specific panel of analyte biomarkers greater than or equal to the reference standard would be less likely to have JIA disease activity and therefore be a candidate for less aggressive therapy.

Reference Therapy for Treatment

In some embodiments, a patient is treated more or less aggressively than a reference therapy. A reference therapy is any therapy that is the standard of care for JIA. The standard of care can vary temporally and geographically, and a skilled person can easily determine the appropriate standard of care by consulting the relevant medical literature.

In some embodiments, based on a determination that levels of a panel of biomarkers is a) greater than, b) less than, c) equal to, d) greater than or equal to, or e) less than or equal to a reference standard, treatment will be either 1) more aggressive, or 2) less aggressive than a standard therapy.

In some embodiments, a more aggressive therapy than the standard therapy comprises beginning treatment earlier than in the standard therapy. In some embodiments, a more aggressive therapy than the standard therapy comprises administering additional treatments than in the standard therapy. In some embodiments, a more aggressive therapy than the standard therapy comprises treating on an accelerated schedule compared to the standard therapy. In some embodiments, a more aggressive therapy than the standard therapy comprises administering additional treatments not called for in the standard therapy.

In some embodiments, a less aggressive therapy than the standard therapy comprises delaying treatment relative to the standard therapy. In some embodiments, a less aggressive therapy than the standard therapy comprises administering less treatment than in the standard therapy. In some embodiments, a less aggressive therapy than the standard therapy comprises administering treatment on a decelerated schedule compared to the standard therapy. In some embodiments, a less aggressive therapy than the standard therapy comprises administering no treatment.

Treating JIA

Treatment strategies can be confounded by the fact that JIA is a classification given to a group of subjects with a diverse array of related symptoms. This suggests that certain subtypes of JIA are driven by specific cell type or cytokine. As a likely consequence, no single therapy has proven optimal for treatment. Given the increasing numbers of therapeutic options available for JIA, the need for an individually tailored treatment directed by immunological prognostic factors of treatment outcome is imperative. In various embodiments of the present teachings, a biomarker-derived algorithm can be used to quantify therapy response in JIA subjects. Measuring biomarker levels over a period time can provide the clinician with a dynamic picture of the subject's biological state, and the DAI scores are highly correlated to JADAS. Overlaying the JADAS score with the DAI score can provide a deeper understanding of how a subject is responding to therapy. These embodiments of the present teachings thus will provide subject-specific biological information, which will be informative for therapy decision and will facilitate therapy response monitoring, and should result in more rapid and more optimized treatment, better control of disease activity, and an increase in the proportion of subjects achieving remission.

Differences in the genetic makeup of subjects can result in differences in their relative abilities to metabolize various drugs, which may modulate the symptoms or state of inflammatory disease. Subjects that have inflammatory disease can vary in age, ethnicity, body mass index (BMI), total cholesterol levels, blood glucose levels, blood pressure, LDL and HDL levels, and other parameters. Accordingly, use of the biomarkers disclosed herein, both alone and together in combination with known genetic factors for drug metabolism, allow for a pre-determined level of predictability that a putative therapeutic or prophylactic to be tested in a selected subject will be suitable for treating or preventing inflammatory disease in the subject.

In one embodiment, the practitioner adjusts the therapy based on a comparison between a reference level and the levels of one or more analyte biomarkers or the levels of a specific panel of analyte biomarkers in a sample from a patient. In one embodiment, the practitioner adjusts the therapy by selecting and administering a different drug. In one embodiment, the practitioner adjusts the therapy by selecting and administering a different combination of drugs. In one embodiment, the practitioner adjusts the therapy by adjusting drug dosage. In one embodiment, the practitioner adjusts the therapy by adjusting dose schedule. In one embodiment, the practitioner adjusts the therapy by adjusting length of therapy. In one embodiment, the practitioner adjusts the therapy by selecting and administering a different drug combination and adjusting drug dosage. In one embodiment, the practitioner adjusts the therapy by selecting and administering a different drug combination and adjusting dose schedule. In one embodiment, the practitioner adjusts the therapy by selecting and administering a different drug combination and adjusting length of therapy. In one embodiment, the practitioner adjusts the therapy by adjusting drug dosage and dose schedule. In one embodiment, the practitioner adjusts the therapy by adjusting drug dosage and adjusting length of therapy. In one embodiment, the practitioner adjusts the therapy by adjusting dose schedule and adjusting length of therapy. In one embodiment, the practitioner adjusts the therapy by selecting and administering a different drug, adjusting drug dosage, and adjusting dose schedule. In one embodiment, the practitioner adjusts the therapy by selecting and administering a different drug, adjusting drug dosage, and adjusting length of therapy. In one embodiment, the practitioner adjusts the therapy by selecting and administering a different drug, adjusting dose schedule, and adjusting length of therapy. In one embodiment, the practitioner adjusts the therapy by adjusting drug dosage, adjusting dose schedule, and adjusting length of therapy. In one embodiment, the practitioner adjusts the therapy by selecting and administering a different drug, adjusting drug dosage, adjusting dose schedule, and adjusting length of therapy.

In some embodiments, treatment comprises a less aggressive therapy than a reference therapy. In one embodiment a less aggressive therapy comprises not administering drugs and taking a "watchful waiting" approach. "Watchful-waiting," also sometimes called "active surveillance," also has its conventional meaning in the art. This generally means observation and regular monitoring without treatment of the underlying disease. Other treatments can be started if symptoms develop, or if there are signs that JIA disease activity is increasing.

In one embodiment a less aggressive therapy comprises delaying treatment. In one embodiment a less aggressive therapy comprises selecting and administering less potent drugs. In one embodiment a less aggressive therapy comprises decreasing the frequency treatment. In one embodiment a less aggressive therapy comprises shortening length of therapy. In one embodiment, less aggressive therapy comprises selecting and administering less potent drugs and decreasing drug dosage. In one embodiment, less aggressive therapy comprises selecting and administering less potent drugs and decelerating dose schedule. In one embodiment, less aggressive therapy comprises selecting and administering less potent drugs and shortening length of therapy. In one embodiment, less aggressive therapy comprises decreasing drug dosage and decelerating dose schedule. In one embodiment, less aggressive therapy comprises decreasing drug dosage and shortening length of therapy. In one embodiment, less aggressive therapy comprises decelerating dose schedule and shortening length of therapy. In one embodiment, less aggressive therapy comprises selecting and administering less potent drugs, decreasing drug dosage, and decelerating dose schedule. In one embodiment, less aggressive therapy comprises selecting and administering less potent drugs, decreasing drug dosage, and shortening length of therapy. In one embodiment, less aggressive therapy comprises selecting and administering less potent drugs, decelerating dose schedule, and shortening length of therapy. In one embodiment, less aggressive therapy comprises decreasing drug dosage, decelerating dose schedule, and shortening length of therapy. In one embodiment, less aggressive therapy comprises selecting and administering less potent drugs, decreasing drug dosage, decelerating dose schedule, and shortening length of therapy. In some embodiments, a less aggressive therapy comprises administering only non-drug-based therapies.

In another aspect of the present application, treatment comprises a more aggressive therapy than a reference therapy. In one embodiment a more aggressive therapy comprises increased length of therapy. In one embodiment a more aggressive therapy comprises increased frequency of the dose schedule. In one embodiment, more aggressive therapy comprises selecting and administering more potent drugs and increasing drug dosage. In one embodiment, more aggressive therapy comprises selecting and administering more potent drugs and accelerating dose schedule. In one embodiment, more aggressive therapy comprises selecting and administering more potent drugs and increasing length of therapy. In one embodiment, more aggressive therapy comprises increasing drug dosage and accelerating dose schedule. In one embodiment, more aggressive therapy comprises increasing drug dosage and increasing length of therapy. In one embodiment, more aggressive therapy comprises accelerating dose schedule and increasing length of therapy. In one embodiment, more aggressive therapy comprises selecting and administering more potent drugs, increasing drug dosage, and accelerating dose schedule. In one embodiment, more aggressive therapy comprises selecting and administering more potent drugs, increasing drug dosage, and increasing length of therapy. In one embodiment, more aggressive therapy comprises selecting and administering more potent drugs, accelerating dose schedule, and increasing length of therapy. In one embodiment, more aggressive therapy comprises increasing drug dosage, accelerating dose schedule, and increasing length of therapy. In one embodiment, more aggressive therapy comprises selecting and administering more potent drugs, increasing drug dosage, accelerating dose schedule, and increasing length of therapy. In some embodiments, a more aggressive therapy comprises administering a combination of drug-based and non-drug-based therapies.

Combination with Clinical Parameters

Any of the aforementioned clinical parameters can also be used in the practice of the present teachings, as input to a formula or as a pre-selection criteria defining a relevant population to be measured using a particular biomarker panel and formula. As noted above, clinical parameters can also be useful in the biomarker normalization and pre-processing, or in selecting particular biomarkers, panel construction, formula type selection and derivation, and formula result post-processing.

Clinical Assessments of the Present Teachings

In some embodiments of the present teachings, panels of biomarkers and formulas are tailored to the population, endpoints or clinical assessment, and/or use that is intended. For example, the biomarker panels and formulas can be used to assess subjects for primary prevention and diagnosis, and for secondary prevention and management. For the primary assessment, the biomarker panels and formulas can be used for prediction and risk stratification for future conditions or disease sequelae, for the diagnosis of inflammatory disease, for the prognosis of disease activity and rate of change, and for indications for future diagnosis and therapeutic regimens. For secondary prevention and clinical management, the biomarker panels and formulas can be used for prognosis and risk stratification. The biomarker panels and formulas can be used for clinical decision support, such as determining whether to defer intervention or treatment, to recommend preventive check-ups for at-risk patients, to recommend increased visit frequency, to recommend increased testing, to recommend intervention, and to recommend therapy withdraw or tapering. The biomarker panels and formulas can also be useful for therapeutic selection, determining response to treatment, adjustment and dosing of treatment, monitoring ongoing therapeutic efficiency, and indication for change in therapeutic regimen.

In some embodiments of the present teachings, the biomarker panels and formulas can be used to aid in the diagnosis of inflammatory disease, and in the determination of the severity of inflammatory disease. The biomarker panels and formulas can also be used for determining the future status of intervention such as, for example in JIA, determining the prognosis of future joint erosion with or without treatment. Certain embodiments of the present teachings can be tailored to a specific treatment or a combination of treatments. X-ray is currently considered the gold standard for assessment of disease progression, but it has limited capabilities since subjects may have long periods of active symptomatic disease while radiographs remain normal or show only nonspecific changes. Conversely, subjects who seem to have quiescent disease (subclinical disease) may continue to progress over time, undetected clinically until significant radiographic damage has occurred. If subjects with a high likelihood of disease progression could be identified in advance, the opportunity for early aggressive treatment could result in much more effective disease outcomes. See, e.g., M. Weinblatt et al., *N. Engl. J. Med.* 1999, 340:253-259. In certain embodiments of the present teachings, an algorithm developed from the biomarkers can be used, with significant power, to characterize the level of bone or cartilage damage activity in JIA subjects. In other embodiments, an algorithm developed from the set of biomarkers can be used, with significant power, to prognose joint destruction over time. In other embodiments, the DAI score can be used as a strong predictor of radiographic or other imaging-based progression, giving the clinician a novel way to identify subjects at risk of JIA-induced joint damage and allowing for early prescription of joint-sparing agents, prophylactically.

In some embodiments of the present teachings, the biomarker panels and formulas can be used as surrogate markers of clinical events necessary for the development of inflammatory disease-specific agents; e.g., pharmaceutical agents. That is, the DAI surrogate marker, derived from a biomarker panel, can be used in the place of clinical events in a clinical trial for an experimental JIA treatment. Biomarker panels and formulas can thus be used to derive an inflammatory disease surrogate endpoint to assist in the design of experimental treatments for JIA.

Measurement of Biomarkers

The quantity of one or more biomarkers of the present teachings can be indicated as a value. The value can be one or more numerical values resulting from the evaluation of a sample, and can be derived, e.g., by measuring level(s) of the biomarker(s) in a sample by an assay performed in a laboratory, or from dataset obtained from a provider such as a laboratory, or from a dataset stored on, e.g., a server. Levels of any particular biomarker can be measured using any of several techniques known in the art for that specific biomarker and assays for individual biomarkers can be combined into panel assays as disclosed herein. The present teachings encompass such techniques, and further include all subject fasting and/or temporal-based sampling procedures for measuring biomarkers.

The actual measurement of levels of a biomarker can be determined at the protein or nucleic acid level using any suitable method known in the art for that biomarker. "Protein" detection comprises detection of full-length proteins, mature proteins, pre-proteins, polypeptides, isoforms, mutations, variants, post-translationally modified proteins and variants thereof, and can be detected in any suitable manner. Levels of biomarkers can be determined at the protein level, e.g., by measuring the serum levels of peptides encoded by the gene products described herein, or by measuring the enzymatic activities of these protein biomarkers. Such methods are well-known in the art for individual biomarkers and include, e.g., immunoassays based on antibodies to proteins encoded by the genes, aptamers or molecular imprints. Any biological material can be used for the detection/quantification of the protein or its activity. Alternatively, a suitable method can be selected to determine the activity of proteins encoded by the biomarker genes according to the activity of each protein analyzed. For biomarker proteins, polypeptides, isoforms, mutations, and variants thereof known to have enzymatic activity, the activities can be determined in vitro using enzyme assays known in the art. Such assays include, without limitation, protease assays, kinase assays, phosphatase assays, reductase assays, among many others. Modulation of the kinetics of enzyme activities can be determined by measuring the rate constant KM using known algorithms, such as the Hill plot, Michaelis-Menten equation, linear regression plots such as Lineweaver-Burk analysis, and Scatchard plot.

Expression of a biomarker can be detected and measured using techniques well-known to those of skill in the art for that biomarker (e.g., using sequence information provided by public database entries for the biomarker). For example, nucleic acid sequences in the sequence databases that correspond to nucleic acids of biomarkers can be used to construct primers and probes for detecting and/or measuring biomarker nucleic acids. These probes can be used in, e.g., Northern or Southern blot hybridization analyses, ribonuclease protection assays, and/or methods that quantitatively amplify specific nucleic acid sequences. As another example, sequences from sequence databases can be used to construct primers for specifically amplifying biomarker sequences in, e.g., amplification-based detection and quantitation methods such as reverse-transcription based polymerase chain reaction (RT-PCR) and PCR. When alterations in gene expression are associated with gene amplification, nucleotide deletions, polymorphisms, post-translational modifications and/or mutations, sequence comparisons in test and reference populations can be made by comparing relative amounts of the examined DNA sequences in the test and reference populations.

As an example, Northern hybridization analysis using probes which specifically recognize one or more of these sequences can be used to determine gene expression. Alternatively, expression can be measured using RT-PCR; e.g., polynucleotide primers specific for the differentially expressed biomarker mRNA sequences reverse-transcribe the mRNA into DNA, which is then amplified in PCR and can be visualized and quantified. Biomarker RNA can also be quantified using, for example, other target amplification methods, such as TMA, SDA, and NASBA, or signal amplification methods (e.g., bDNA), and the like. Ribonuclease protection assays can also be used, using probes that specifically recognize one or more biomarker mRNA sequences, to determine gene expression.

Alternatively, biomarker protein and nucleic acid metabolites can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. See WO 04/056456 and WO 04/088309, each of which is hereby incorporated by reference in its entirety. In this regard, other biomarker analytes can be measured using the above-mentioned detection methods, or other methods known to the skilled artisan. For example, circulating calcium ions ($Ca^{2+}$) can be detected in a sample using fluorescent dyes such as the Fluo series, Fura-2A, Rhod-2, among others. Other biomarker metabolites can be similarly detected using reagents that are specifically designed or tailored to detect such metabolites.

In some embodiments, a biomarker can be detected by contacting a subject sample with reagents, generating complexes of reagent and analyte, and detecting the complexes. Examples of "reagents" include but are not limited to nucleic acid primers and antibodies.

In some embodiments of the present teachings an antibody binding assay is used to detect a biomarker; e.g., a sample from the subject is contacted with an antibody reagent that binds the biomarker analyte, a reaction product (or complex) comprising the antibody reagent and analyte is generated, and the presence (or absence) or amount of the complex is determined. The antibody reagent useful in detecting biomarker analytes can be monoclonal, polyclonal, chimeric, recombinant, or a fragment of the foregoing, as discussed in detail above, and the step of detecting the reaction product can be carried out with any suitable immunoassay. The sample from the subject is typically a biological fluid as described above, and can be the same sample of biological fluid as is used to conduct the method described above.

Immunoassays carried out in accordance with the present teachings can be homogeneous assays or heterogeneous assays. In a homogeneous assay the immunological reaction can involve the specific antibody (e.g., anti-biomarker protein antibody), a labeled analyte, and the sample of interest. The label produces a signal, and the signal arising from the label becomes modified, directly or indirectly, upon binding of the labeled analyte to the antibody. Both the immunological reaction of binding, and detection of the extent of binding, can be carried out in a homogeneous solution. Immunochemical labels which can be employed include but are not limited to free radicals, radioisotopes, fluorescent dyes, enzymes, bacteriophages, and coenzymes. Immunoassays include competition assays.

In a heterogeneous assay approach, the reagents can be the sample of interest, an antibody, and a reagent for producing a detectable signal. Samples as described above can be used. The antibody can be immobilized on a support, such as a bead (such as protein A and protein G agarose beads), plate or slide, and contacted with the sample suspected of containing the biomarker in liquid phase. The support is separated from the liquid phase, and either the support phase or the liquid phase is examined using methods known in the art for detecting signal. The signal is related to the presence of the analyte in the sample. Methods for producing a detectable signal include but are not limited to the use of radioactive labels, fluorescent labels, or enzyme labels. For example, if the antigen to be detected contains a second binding site, an antibody which binds to that site can be conjugated to a detectable (signal-generating) group and added to the liquid phase reaction solution before the separation step. The presence of the detectable group on the solid support indicates the presence of the biomarker in the test sample. Examples of suitable immunoassays include but are not limited to oligonucleotides, immunoblotting, immunoprecipitation, immunofluorescence methods, chemiluminescence methods, electrochemiluminescence (ECL), and/or enzyme-linked immunoassays (ELISA).

Those skilled in the art will be familiar with numerous specific immunoassay formats and variations thereof which can be useful for carrying out the method disclosed herein. See, e.g., E. Maggio, *Enzyme-Immunoassay* (1980), CRC Press, Inc., Boca Raton, Fla. See also U.S. Pat. No. 4,727,022 to C. Skold et al., titled "Novel Methods for Modulating Ligand-Receptor Interactions and their Application"; U.S. Pat. No. 4,659,678 to G C Forrest et al., titled "Immunoassay of Antigens"; U.S. Pat. No. 4,376,110 to GS David et al., titled "Immunometric Assays Using Monoclonal Antibodies"; U.S. Pat. No. 4,275,149 to D. Litman et al., titled "Macromolecular Environment Control in Specific Receptor Assays"; U.S. Pat. No. 4,233,402 to E. Maggio et al., titled "Reagents and Method Employing Channeling"; and, U.S. Pat. No. 4,230,797 to R. Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein can likewise be conjugated to detectable labels or groups such as radiolabels (e.g., 35S, 125I, 131I), enzyme labels (e.g., horseradish peroxidase, alkaline phosphatase), and fluorescent labels (e.g., fluorescein, Alexa, green fluorescent protein, rhodamine) in accordance with known techniques.

Antibodies may also be useful for detecting post-translational modifications of biomarkers. Examples of post-translational modifications include, but are not limited to tyrosine phosphorylation, threonine phosphorylation, serine phosphorylation, citrullination and glycosylation (e.g., O-GlcNAc). Such antibodies specifically detect the phosphorylated amino acids in a protein or proteins of interest, and can be used in the immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF). See U. Wirth et al., *Proteomics* 2002, 2(10): 1445-1451.

Reports

In some embodiments, a report is prepared in a format that is capable of being disseminated to the subject or a caregiver of the subject that provides information allow the subject or caregiver to make decisions based on the diagnosis Kits Other embodiments of the present teachings comprise biomarker detection reagents packaged together in the form of a kit for conducting any of the assays of the present teachings. In certain embodiments, the kits comprise oligonucleotides that specifically identify one or more biomarker nucleic acids based on homology and/or complementarity with biomarker nucleic acids. The oligonucleotide sequences may correspond to fragments of the biomarker nucleic acids. For example, the oligonucleotides can be more than 200, 200, 150, 100, 50, 25, 10, or fewer than 10 nucleotides in length. In other embodiments, the kits comprise antibodies to proteins encoded by the biomarker nucleic acids. The kits of the present teachings can also comprise aptamers. The kit can contain in separate containers a nucleic acid or antibody (the antibody either bound to a solid matrix, or packaged separately with reagents for binding to a matrix), control formulations (positive and/or negative), and/or a detectable label, such as but not limited to fluorescein, green fluorescent protein, rhodamine, cyanine dyes, Alexa dyes, luciferase, and radiolabels, among others. Instructions for carrying out the assay, including, optionally, instructions for generating a DAI score, can be included in the kit; e.g., written, tape, VCR, or CD-ROM. The assay can for example be in the form of a Northern hybridization or a sandwich ELISA as known in the art.

In some embodiments of the present teachings, biomarker detection reagents can be immobilized on a solid matrix, such as a porous strip, to form at least one biomarker detection site. In some embodiments, the measurement or detection region of the porous strip can include a plurality of sites containing a nucleic acid. In some embodiments, the test strip can also contain sites for negative and/or positive controls. Alternatively, control sites can be located on a separate strip from the test strip. Optionally, the different detection sites can contain different amounts of immobilized nucleic acids, e.g., a higher amount in the first detection site and lesser amounts in subsequent sites. Upon the addition of test sample, the number of sites displaying a detectable signal provides a quantitative indication of the amount of biomarker present in the sample. The detection sites can be configured in any suitably detectable shape and can be, e.g., in the shape of a bar or dot spanning the width of a test strip.

In other embodiments of the present teachings, the kit can contain a nucleic acid substrate array comprising one or more nucleic acid sequences. The nucleic acids on the array specifically identify one or more nucleic acid sequences represented by the biomarkers. In various embodiments, the expression of one or more of the sequences represented by the biomarkers can be identified by virtue of binding to the array. In some embodiments the substrate array can be on a solid substrate, such as what is known as a "chip." See, e.g., U.S. Pat. No. 5,744,305. In some embodiments the substrate array can be a solution array; e.g., xMAP (Luminex, Austin, Tex.), Cyvera (Illumina, San Diego, Calif.), RayBio Antibody Arrays (RayBiotech, Inc., Norcross, Ga.), CellCard (Vitra Bioscience, Mountain View, Calif.) and Quantum Dots' Mosaic (Invitrogen, Carlsbad, Calif.).

Machine-Readable Storage Medium

A machine-readable storage medium can comprise, for example, a data storage material that is encoded with machine-readable data or data arrays. The data and machine-readable storage medium are capable of being used for a variety of purposes, when using a machine programmed with instructions for using said data. Such purposes include, without limitation, storing, accessing and manipulating information relating to the inflammatory disease activity of a subject or population over time, or disease activity in response to inflammatory disease treatment, or for drug discovery for inflammatory disease, etc. Data comprising measurements of the biomarkers of the present teachings, and/or the evaluation of disease activity or disease state from these biomarkers, can be implemented in computer programs that are executing on programmable computers, which comprise a processor, a data storage system, one or more input devices, one or more output devices, etc. Program code can be applied to the input data to perform the functions described herein, and to generate output information. This output information can then be applied to one or more output devices, according to methods well-known in the art. The computer can be, for example, a personal computer, a microcomputer, or a workstation of conventional design.

The computer programs can be implemented in a high-level procedural or object-oriented programming language, to communicate with a computer system such as for example, the computer system illustrated in FIG. 10. The programs can also be implemented in machine or assembly language. The programming language can also be a compiled or interpreted language. Each computer program can be stored on storage media or a device such as ROM, magnetic diskette, etc., and can be readable by a programmable computer for configuring and operating the computer when the storage media or device is read by the computer to perform the described procedures. Any health-related data management systems of the present teachings can be considered to be implemented as a computer-readable storage medium, configured with a computer program, where the storage medium causes a computer to operate in a specific manner to perform various functions, as described herein.

The biomarkers disclosed herein can be used to generate a "subject biomarker profile" taken from subjects who have inflammatory disease. The subject biomarker profiles can then be compared to a reference biomarker profile, in order to diagnose or identify subjects with inflammatory disease, to monitor the progression or rate of progression of inflammatory disease, or to monitor the effectiveness of treatment for inflammatory disease. The biomarker profiles, reference and subject, of embodiments of the present teachings can be contained in a machine-readable medium, such as analog tapes like those readable by a CD-ROM or USB flash media, among others. Such machine-readable media can also contain additional test results, such as measurements of clinical parameters and clinical assessments. The machine-readable media can also comprise subject information; e.g., the subject's medical or family history. The machine-readable media can also contain information relating to other disease activity algorithms and computed scores or indices, such as those described herein.

EXAMPLES

Aspects of the present teachings can be further understood in light of the following examples, which should not be construed as limiting the scope of the present teachings in any way.

The practice of the present teachings employ, unless otherwise indicated, conventional methods of protein chemistry, biochemistry, recombinant DNA techniques and pharmacology, within the skill of the art. Such techniques are explained fully in the literature. See, e.g., T. Creighton, *Proteins: Structures and Molecular Properties,* 1993, W. Freeman and Co.; A. Lehninger, Biochemistry, Worth Publishers, Inc. (current addition); J. Sambrook et al., *Molecular Cloning: A Laboratory Manual,* 2nd Edition, 1989; Methods In *Enzymology,* S. Colowick and N. Kaplan, eds., Academic Press, Inc.; *Remington's Pharmaceutical Sciences,* 18th Edition, 1990, Mack Publishing Company, Easton, Pa.; Carey and Sundberg, *Advanced Organic Chemistry,* Vols. A and B, 3rd Edition, 1992, Plenum Press.

The practice of the present teachings also employ, unless otherwise indicated, conventional methods of statistical analysis, within the skill of the art. Such techniques are explained fully in the literature. See, e.g., J. Little and D. Rubin, *Statistical Analysis with Missing Data,* 2nd Edition 2002, John Wiley and Sons, Inc., NJ; M. Pepe, *The Statistical Evaluation of Medical Tests for Classification and Prediction* (*Oxford Statistical Science Series*) 2003, Oxford University Press, Oxford, UK; X. Zhoue et al., *Statistical Methods in Diagnostic Medicine* 2002, John Wiley and Sons, Inc., NJ; T. Hastie et. al, *The Elements of Statistical Learning: Data Mining, Inference, and Prediction,* Second Edition 2009, Springer, N.Y.; W. Cooley and P. Lohnes, *Multivariate procedures for the behavioral science* 1962, John Wiley and Sons, Inc. NY; E. Jackson, *A User's Guide to Principal Components* 2003, John Wiley and Sons, Inc., NY.

Example 1

Identification of Serum Protein Biomarkers Associated with JIA

Candidate biomarkers were evaluated for association with the Juvenile Disease Activity Score (JADAS) or the 1997 American College of Rheumatology pediatric improvement criteria (ACR). The first set of candidate markers includes the 12 biomarkers of the VECTRA™ DA test (VCAM-1, EGF, VEGF-A, IL-6, TNF-R1, MMP-1, MMP-3, YKL-40, Leptin, Resistin, SAA, and CRP). The VECTRA™ DA biomarkers are described in detail in U.S. patent application Ser. No. 12/905,984, which is hereby incorporated by reference in its entirety. In brief, the VECTRA™ DA multi-biomarker assay measures levels of the 12 biomarkers and uses a pre-specified algorithm to generate a multi-biomarker disease activity score (MBDS score) ranging from 1-100. The MBDA score has demonstrated strong correlations with rheumatoid arthritis (RA) clinical disease activity in multiple cohorts (Bakker et al. *Annals of the Rheumatic Diseases* 71:1692-7 (2012); Curtis et al. *arthritis care & research* 64:1794-803 (2012)). Although VECTRA™ DA was initially developed for RA disease progression, many categories of JIA are histologically and biologically similar to RA. Such categories include polyarticular JIA (RF negative and positive) and extended oligoarticular JIA (Ravelli and Martini, *Lancet* 369:767-778 (2007); Petty et al. *J. Rheumatology* 31:390-392 (2004)).

The 12 Vectra™ DA biomarkers are listed in Table 2.

TABLE 2

| Biomarker symbol | NCBI RefSeq |
| --- | --- |
| VCAM-1 | NP_001069.1 |
| EGF | NP_001954.2 |
| VEGF-A | NP_001020539.2 |
| IL-6 | NP_00591.1 |
| TNF-R1 | NP_001056.1 |
| MMP-1 | NP_002412.1 |
| MMP-3 | NP_002413.1 |
| YKL-40 | NP_001267.2 |
| Leptin | NP_000221.1 |
| Resistin | NP_065148.1 |
| SAA | NP_000322.2 |
| CRP | NP_000558.2 |

Assays additional biomarkers in addition to the 12 VECTRA™ DA biomarkers, some of which are listed in Table 3.

TABLE 3

| Adhesion Molecules | Growth Factors | Cytokines/ Chemokines | Matrix Metallo-proteinases | Skeletal-related Proteins | Acute Phase Proteins | Other |
| --- | --- | --- | --- | --- | --- | --- |
| ICAM-1 | TRAP1 | IL-1B | MMP-9 | PYD | SAP | Calprotectin |
| P-selectin | | IL-8 | TIMP-1 | | | S100 A12 |
| L-selectin | | IL-10 | | | | S100 A14 |
| | | IL-18 | | | | HSP60 |
| | | IL-17 | | | | A2M |
| | | IL-21 | | | | ATIII |
| | | BAFF | | | | HP |
| | | CCL2 | | | | AGP1 |
| | | CCL3 | | | | MF |
| | | CCL11 | | | | TP53 |
| | | CXCL9 | | | | ATM |
| | | CXCL10 | | | | GZM |
| | | CCL22 | | | | TTR |
| | | TNF-R1 | | | | CFH |
| | | IL-6R | | | | Complement C3 |
| | | CD40LG | | | | Complement C4 |
| | | | | | | GSN |

Table 2: Candidate Biomarkers

Serum samples were obtained at the point of care and at the time of routine clinical blood draws from ninety individuals covering a wide spectrum of disease activity from three categories of JIA (polyarticular RF+, polyarticular RF−, and extended oligoarticular). Table 3 summarizes the clinical characteristics of the cohort (see also Table YY submitted with U.S. Provisional Application No. 61/974,390, filed on Apr. 2, 2014, which is herein incorporated by reference in its entirety).

TABLE 4

| Total Number (N) | 90 |
| --- | --- |
| Age, Median (Range) | 12 (3-18) |
| Female (n) | 73 |
| Male (n) | 17 |
| Extended Oligoarticular (n) | 19 |
| Polyarticular (n) | 71 |
| RF (−) at baseline (n) | 62 |
| RF (+) at baseline (n) | 20 |
| Patients on therapy (n) | 31 |
| ESR Median (Range) (mm/hr) | 10 (2-102) |
| Physician's Global Assessment Median (Range) | 2 (0-10) |
| Parent's Global Assessment Median (Range) | 2 (0-9) |
| JADAS Median (Range) | 7 (0-32) |
| MBDA Median (Range) | 19 (11-92) |

All biomarker assays except Calprotectin assays were performed at controlled ambient temperature of 20±5° C. Multispot 96-well plates (MSD) were spotted in specific locations with biomarker-specific capture antibodies for. Biomarker concentrations were determined using 3 separate multiplex panels, based on sample dilution requirements. Prediluted standards and QC run controls were loaded onto the plate alongside diluted patient samples and diluted process controls. Diluted serum samples and process controls were prepared using a validated Hamilton STAR (Reno, Nev., USA) automated dilution platform. Calprotectin assays was performed using standard ELISA.

The VECTRA™ DA biomarkers were assayed to determine measurability. To establish the assay's dynamic range for each biomarker, the limit of quantitation (LOQ), defined as the actual amount of analyte that can be reliably detected in a sample and at which the total analytical error meets the requirements for accuracy and precision, was determined as described in EP17-A Clinical Laboratory Standards Institute (CLSI). Acceptable accuracy at the LOQ was defined as 80-120% recovery of the input mass based on the vendor's specification for each particular protein, and the acceptable precision requirement at the LOQ was defined as a 20% CV. An assay's analytical measurable range was defined as the difference between the upper limit (ULOQ) and the lower limit (LLOQ). The clinically reportable or dynamic range for an assay was defined as the dilution-adjusted range. Non-VECTRA™ DA biomarkers were analyzed via commercially available standard ELISAs.

Univariate Analysis

For intra-run precision of an MBDA score, 4 serum pools were each run 14 times on a single plate. Two plates from each of 2 different lots were evaluated, and the means and % CVs for the MBDA score were calculated. Associations were calculated between the MBDS scores and JADAS scores, Physician's Global Assessment, Parent Assessment of Child's Global Health, and total Number of Joints with Active Arthritis and ESR (see FIG. 3 and Table YY submitted with U.S. Provisional Application No. 61/974,390, filed on Apr. 2, 2014, which is herein incorporated by reference in its entirety). The correlation results were then compared using univariate analysis.

The most informative biomarkers for overall assessment of JIA disease activity were then chosen. An importance score was generated for each biomarker through an array of univariate and multivariate analyses. Univariate analysis was performed to evaluate the correlation between each individual biomarker and each clinical measure.

JADAS Scoring

Samples acquired from the cohorts described above were analyzed using the 18 biomarker panel. The Juvenile Arthritis Disease Activity Score (JADAS) based on 10 joints was calculated for each sample, and each sample was classified as clinically inactive disease or active disease using the ACR provisional criteria for clinically inactive disease (CID).

A strong correlation between the 12 biomarker VECTRA™ DA MBDA panel score and JADAS was observed at r=0.77 (FIG. 1). There was also a high degree of correlation between the 12 biomarker VECTRA™ DA MBDA panel score with JADAS components. For example, the correlation between the 12 biomarker VECTRA™ DA MBDA panel score and the Physician's Global Assessment was r=0.71; the correlation between the 12 biomarker VECTRA™ DA MBDA panel and the Parent's Global Assessment was r=0.61; and the correlation between the 12 biomarker VECTRA™ DA MBDA panel and Active Joint Counts was r=0.62 (FIG. 1).

There was a further strong correlation between a 9 or 10 biomarker panel comprising IL-6, MMP3, CRP, TNF-R1, with or w/o Calprotectin, YKL-40, ICAM-1, SAA, VCAM-1 and MMP1. Use of different algorithms further demonstrated strong correlations between MBDA and JADAS. FIG. 2 demonstrates that this panel shows that the correlation between the 9 or 10 biomarker panel with or without Calprotectin and JADAS was r=0.85 (top panels). Furthermore FIG. 2 demonstrates that the 10 biomarker panel with Calprotectin and the Physician's Global Assessment was r=0.80 (lower left panel), and the 9 biomarker panel without Calprotectin and the Physician's Global Assessment was r=0.81 (lower right panel).

Additionally, several individual biomarkers, including IL-6, MMP-3, TNF-R1, Calprotectin and YKL-40, exhibited higher concentrations in the active disease group compared with the CID group (FIG. 3).

Figure 4:
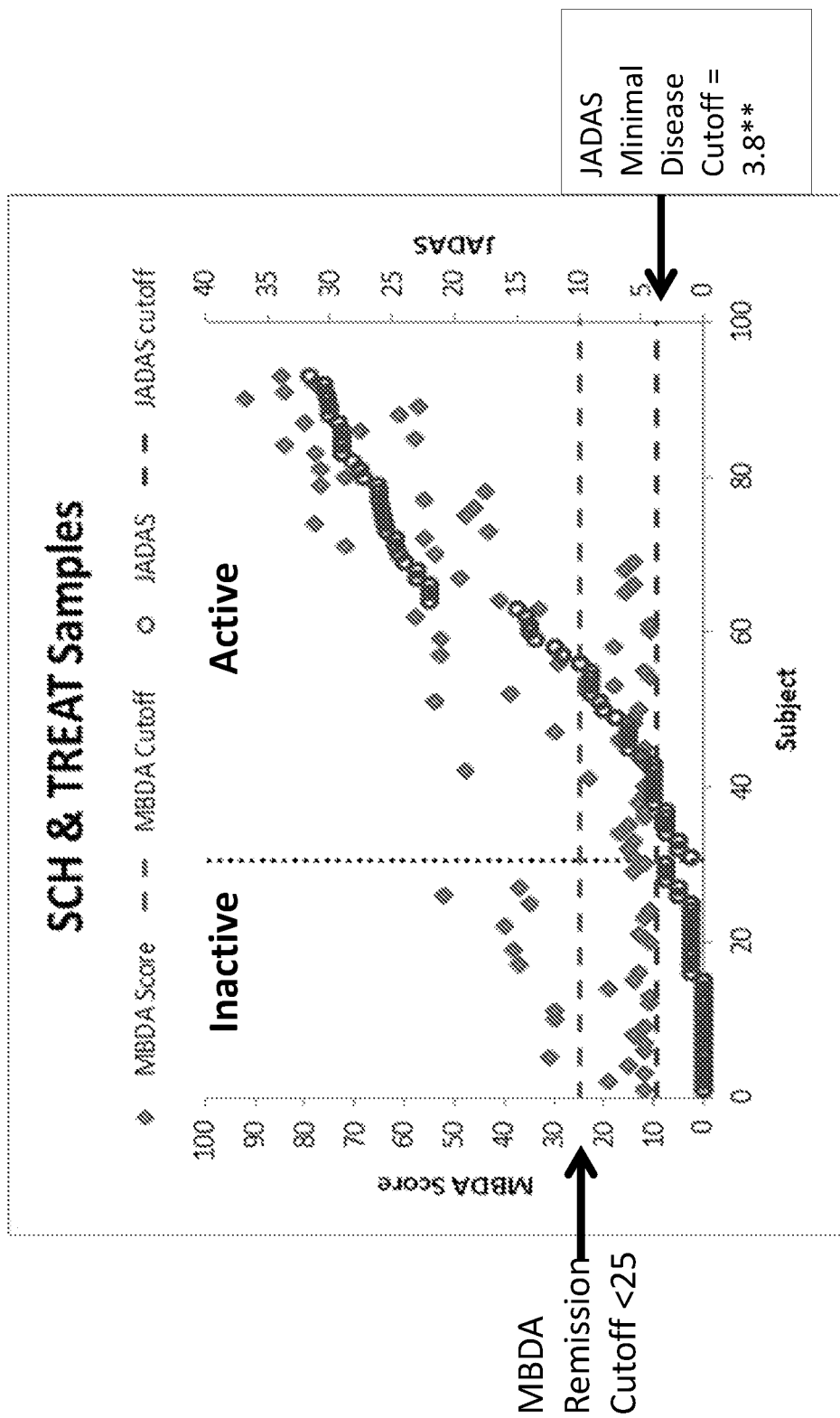
FIG. 4 illustrates Inactive Disease vs. Active Disease. Paired VECTRA™ DA MBDA and JADAS values for individual subjects presented as a function of ACR disease.

Using the ACR provisional criteria for defining clinical inactive vs. active disease, JADAS10 scores and MBDA scores were compared for each of the individual subjects. In the inactive disease group, MBDA identified nine subjects with elevated MBDA scores, indicating a continuing level of biological disease activity in these subjects. Conversely, those subjects with high active disease were comparable with MBDA and JADAS (FIG. 4).

The performance of the biomarkers were further evaluated as a function of ACR disease status and compared to a set of 59 unaffected individual 18 years of age. The mean and median MBDA scores for the normal controls were 14 and 17, respectively. For the ACR inactive disease group (n=18) mean and median MBDA scores were 14 and 21, and the active disease group (n=6) were 36 and 39. The level of the biomarkers is presented in FIG. 5 as the percentile of the InFoRM RA population. The biomarker profiles for the normal population and ACR inactive disease populations appear very similar. In contrast, individual biomarkers, such as SAA, CRP, IL-6, and MMP-3, were elevated in the active disease group and unaffected normal relative to active disease (see also Table ZZ submitted with U.S. Provisional Application No. 61/974,390, filed on Apr. 2, 2014, which is herein incorporated by reference in its entirety).

The invention claimed is:

1. A method for treating a subject having juvenile idiopathic arthritis (JIA) the method comprising:
   providing a test sample comprising a sample of bodily fluid taken from the subject;
   determining a sample concentration for a combination of three or more biomarkers selected from the group comprising C-reactive protein (CRP); epidermal growth factor (EGF); interleukin 6 (IL-6); leptin (LEP); matrix metalloproteinase-1 (MMP1); matrix metalloproteinase-3 (MMP3); resistin (RETN); serum amyloid (SAA); tumor necrosis factor receptor, type 1 (TNF-R1); vascular cell adhesion molecule-1 (VCAM1); vascular endothelial growth factor A (VEGF-A); and YKL-40;
   calculating, using the sample concentrations, a JIA disease activity significantly greater than found for a combination of concentrations of corresponding control biomarkers that are indicative of JIA; and
   administering a JIA therapeutic regimen, wherein the therapeutic regimen comprises administering a therapeutic compound selected from DMARDs, biologic DMARDs, non-steroidal anti-inflammatory drugs (NSAID's), and corticosteroids, or administering physical therapy, dietary modification and/or supplementation, or administering bariatric surgical intervention.

2. The method of claim 1 wherein the biomarkers comprise VCAM-1, EGF, VEGF-A, IL-6, TNF-R1, MMP1, MMP3, YKL-40, Leptin, Resistin, SAA, and CRP.

3. The method of claim 1 where the biomarkers comprise IL-6, MMP3, CRP, TNF-R1, YKL-40, ICAM-1, SAA, VCAM-1 and MMP1.

4. The method of claim 1 wherein the sample concentrations for the subject are predictive of a clinical assessment.

5. The method of claim 4 wherein said clinical assessment is selected from the group consisting of physician global assessment of disease activity (MD global), parent/child global assessment of well-being (PGA), child/parent health assessment questionnaire (CHAR), active arthritic joint counts, Westergren erythrocyte sedimentation rate (ESR), and juvenile arthritis disease activity score (JADAS).

6. The method of claim 1 wherein said JIA is selected from the group consisting of oligoarticular JIA, polyarticular rheumatoid factor (RF) positive JIA, polyarticular RF negative JIA, systemic JIA, psoriatic JIA, enthesitis-related arthritis, and undifferentiated arthritis.

7. The method of claim 1 where the subject has received a treatment for JIA, and further determining efficacy of the treatment based on additional calculation of JIA disease activity.

* * * * *